US008798345B2

(12) United States Patent
Sasaki et al.

(10) Patent No.: US 8,798,345 B2
(45) Date of Patent: Aug. 5, 2014

(54) DIAGNOSIS PROCESSING DEVICE, DIAGNOSIS PROCESSING SYSTEM, DIAGNOSIS PROCESSING METHOD, DIAGNOSIS PROCESSING PROGRAM AND COMPUTER-READABLE RECORDING MEDIUM, AND CLASSIFICATION PROCESSING DEVICE

(75) Inventors: Takahiro Sasaki, Osaka (JP); Satoru Kishida, Tottori (JP); Kentaro Kinoshita, Tottori (JP)

(73) Assignees: Sharp Kabushiki Kaisha, Osaka-shi, Osaka (JP); National University Corporation Tottori University, Tottori-shi, Tottori (JP)

(*) Notice: Subject to any disclaimer, the term of this patent is extended or adjusted under 35 U.S.C. 154(b) by 239 days.

(21) Appl. No.: 13/496,391

(22) PCT Filed: Aug. 16, 2010

(86) PCT No.: PCT/JP2010/063812
§ 371 (c)(1),
(2), (4) Date: Mar. 15, 2012

(87) PCT Pub. No.: WO2011/033890
PCT Pub. Date: Mar. 24, 2011

(65) Prior Publication Data
US 2012/0183187 A1    Jul. 19, 2012

(30) Foreign Application Priority Data

Sep. 17, 2009   (JP) .................................. 2009-215843

(51) Int. Cl.
*G06K 9/00*    (2006.01)
*G06K 9/62*    (2006.01)

(52) U.S. Cl.
USPC ......................................... 382/128; 382/157

(58) Field of Classification Search
USPC ........................................................ 600/408
See application file for complete search history.

(56) References Cited

U.S. PATENT DOCUMENTS

| 5,491,627 | A | | 2/1996 | Zhang et al. |
| 6,058,322 | A | * | 5/2000 | Nishikawa et al. ........... 600/408 |
| 6,396,953 | B1 | * | 5/2002 | Abbey ......................... 382/218 |

(Continued)

FOREIGN PATENT DOCUMENTS

| JP | 6-343627 | 12/1994 |
| JP | 8-96125 | 4/1996 |

(Continued)

OTHER PUBLICATIONS

International Search Report mailed Nov. 16, 2010, directed to International Application No. PCT/JP2010/063812; 4 pages.

*Primary Examiner* — Amara Abdi
(74) *Attorney, Agent, or Firm* — Morrison & Foerster LLP

(57) ABSTRACT

A diagnosis processing device is provided in which diagnosis is realizable by a simple arrangement. A diagnosis processing device (1) of the present invention includes: a learning pattern creating section (10a) for creating a learning pattern by sampling data from a learning image in which abnormality information indicating a substantive feature of abnormality of a target is pre-known; a learning processing section (12) for causing a neural network (17) to learn, by using learning patterns; a diagnostic pattern creating section (10b) for creating a diagnostic pattern by sampling data from a diagnostic image in which abnormality information is unknown; a determination processing section (18) for determining a substantive feature of the abnormality of the target indicated in the abnormality information in the diagnostic image, based on an output value outputted, in response to an input of the diagnostic pattern, from a learned neural network (17) which is a neural network subjected to learning.

16 Claims, 18 Drawing Sheets

(56) References Cited

U.S. PATENT DOCUMENTS

| | | | |
|---|---|---|---|
| 2002/0065460 A1* | 5/2002 | Murao | 600/425 |
| 2004/0254763 A1* | 12/2004 | Sakai et al. | 702/184 |
| 2005/0020903 A1 | 1/2005 | Krishnan et al. | |
| 2005/0049497 A1 | 3/2005 | Krishnan et al. | |
| 2005/0059876 A1 | 3/2005 | Krishnan et al. | |
| 2005/0209519 A1 | 9/2005 | Krishnan et al. | |
| 2008/0226145 A1 | 9/2008 | Moriya | |
| 2008/0240532 A1* | 10/2008 | Carneiro et al. | 382/131 |

FOREIGN PATENT DOCUMENTS

| | | | | |
|---|---|---|---|---|
| JP | 08-096125 | * | 4/1996 | G06T 5/00 |
| JP | 2001-511372 | | 8/2001 | |
| JP | 2002-330951 | | 11/2002 | |
| JP | 2005-245830 | * | 9/2005 | A61B 6/03 |
| JP | 2007-18176 | | 1/2007 | |
| JP | 2007-524461 | | 8/2007 | |
| JP | 2008-212396 | | 9/2008 | |
| WO | WO-2008/017991 | | 2/2008 | |

* cited by examiner

DIAGNOSIS PROCESSING DEVICE, DIAGNOSIS PROCESSING SYSTEM, DIAGNOSIS PROCESSING METHOD, DIAGNOSIS PROCESSING PROGRAM AND COMPUTER-READABLE RECORDING MEDIUM, AND CLASSIFICATION PROCESSING DEVICE

REFERENCE TO RELATED APPLICATIONS

This application is the national stage under 35 USC 371 of International Application No. PCT/JP2010/063812, filed Aug. 16, 2010, which claims priority from Japanese Patent Application No. 2009-215843, filed Sep. 17, 2009, the entire contents of which are incorporated herein by reference.

FIELD OF THE INVENTION

The present invention relates to (i) a diagnosis processing device, (ii) a diagnosis processing system, (iii) a diagnosis processing method, (iv) a diagnosis processing program, and (v) a computer-readable storage medium in which the diagnosis processing program is stored, each of which (i) through (iv) is capable of, by use of a neural network, diagnosing abnormality by image diagnosis in which a chest radiograph or the like, for example, is used.

The present invention relates also to a classification processing device capable of carrying out image classification in a broad field of image processing.

BACKGROUND OF THE INVENTION

In a medical field, for example, image diagnosis using radiographs and the like are used. Conventionally, the image diagnosis requires a doctor to visually check diagnostic images piece by piece in order to determine whether there is abnormality or not. As such, if a conventional image diagnosis is followed, then it is clear that heavier workload is imposed on a doctor.

Recently, studies have been actively conducted in an effort to build a neural network modeling a human brain function and use it in a field of image diagnosis. For example, Patent Literature 1 discloses a novel and excellent method and system for detecting a micro-calcified substance by inspection of a digital breast radiograph.

In the method of Patent Literature 1 and the like, an abnormal region (region of interest) in a digital chest radiograph, which corresponds to an organ/tissue suspected of having a micro-calcified substance, is extracted at first. Then, the region of interest is converted into numerical data, which are then inputted to a neural network learned to detect a micro-calcified substance. In response, a result of detecting and the region of interest are outputted from the neural network.

The micro-calcified substance detecting method etc. extracts the regions of interest in advance, thereby making it possible to attain a decrease in a number of false positive regions, while keeping all true positive regions.

Citation List

Patent Literature 1
Japanese Patent Application Publication, Tokukaihei, No. 6-343627 A (Publication Date: Dec. 20, 1994)

SUMMARY OF INVENTION

Like the method of Patent Literature 1 and the like, it is possible, by use of the neural network which is pre-learned to determine whether there is abnormality or not, to cause a computer to check whether there is abnormality or not at first. As such, a doctor is required to check only regions detected as having the abnormality. This can realize a medical support system in which workload of the doctor can be reduced.

However, in such medical support system, it is normally the case that regions of interest suspected of having abnormality are (i) extracted from data sampled from a radiograph or the like and (ii) inputted to the neural network, so that whether there is abnormality or not is detected for each of the regions of interest.

Generally, extracting of such regions of interest causes increase in complexity and size of a system. However, no case has been reported that whether there is the abnormality or not is determined by inputting data sampled from an entire image to the neural network.

The present invention is made in view of the problem, and an object of the present invention is to provide (i) a diagnosis processing device, (ii) a diagnosis processing system, (iii) a diagnosis processing method, (iv) a diagnosis processing program, (v) a computer-readable storage medium storing therein the diagnosis processing program, and (vi) a classification processing device, each of which (i) through (vi) is capable of realizing diagnosis by use of a simple arrangement.

In order to attain the object, a diagnosis processing device of the present invention is a diagnosis processing device for diagnosing a target for abnormality by use of a neural network, the diagnosis processing device including: learning pattern creating means for creating a learning pattern by (i) digitalizing a learning image into digital data, the learning image being an image in which abnormality information indicating a substantive feature of the abnormality of the target is pre-known, and (ii) sampling data from the digital data of the learning image by use of a predetermined sampling method, the learning pattern indicating a data sequence of a sample data row of the data thus sampled; learning processing means for causing the neural network to learn, by use of two or more learning patterns created as above by the learning pattern creating means; diagnostic pattern creating means for creating a diagnostic pattern by (iii) digitalizing a diagnostic image into digital data, the diagnostic image being an image in which abnormality information is unknown, and (iv) sampling data from the digital data of the diagnostic image by use of the predetermined sampling method, the diagnostic pattern indicating a data sequence of a sample data row of the data thus sampled; and determining means for determining a substantive feature of the abnormality of the target indicated in the abnormality information in the diagnostic image, based on an output value outputted, in response to an input of the diagnostic pattern, from a learned neural network which is the neural network subjected to learning.

In the diagnosis processing device, the learning pattern creating means uses, as the learning image, the diagnosis image in which the abnormality information indicating the substantive feature of the abnormality of the diagnosis target is pre-known by a user, and digitalizes the learning image into the digital data. Then, the learning pattern creating means samples the data from the digital data of the learning image by use of the predetermined sampling method. For example, in a case where reference directions are determined based on a shape feature of a diagnosis target part, which is the diagnosis target in the learning image, the data are sampled the digital image of the learning image in a longitudinal direction out of the reference directions. Then, the learning pattern creating means creates the learning pattern from the data thus sampled.

The learning processing means causes the neural network to learn, by using the two or more learning patterns created as above by the learning pattern creating means. This causes the neural network to become the learned neural network.

The diagnosis pattern creating means digitalize the diagnostic image, in which the abnormality information is unknown by the user, into the digital data and samples the data from the digital data of the diagnostic image by use of the sampling method same as the sampling method used by the learning pattern creating means. Then, the diagnostic pattern creating means creates the diagnostic pattern from the data thus sampled.

After the input of the diagnostic pattern to the learned neural network causes the output of the output value, the determining means determines, based on the output value, the substantive feature of the abnormality of the diagnosis target indicated in the abnormality information in the diagnostic image, and then provides a result of determining to the user.

In this way, the diagnosis processing device can digitalize the diagnostic image into the digital data, sample the data from the digital data of the diagnostic image and create the diagnostic pattern, and determine the substantive feature of the abnormality of the diagnosis target indicated in the abnormality information in the diagnostic image.

This eliminates the need for an arrangement conventionally required for extracting of a suspicious region of interest from the diagnostic in advance. As such, it is possible to realize a diagnosis processing device having a simpler arrangement.

Conventionally, in order to extract the suspicious region of interest from the diagnostic image, it is necessary to collect entire data in the diagnostic image and use such large amount of the data. This gives a rise to a problem that load of arithmetic processing is very heavy.

In contrast, in the diagnosis processing device, it is not necessary to use the entire data. As such, it is possible to attain a great decrease in the load of the arithmetic processing. This is because, in the diagnosis processing device, it is possible to (i) create, for example, two or more patterns made up of respective two or more data rows sampled from the diagnostic image, (ii) carry out arithmetic processing of the neural network by using the two or more patterns thus created, and (iii), after the abnormality of the diagnosis target is detected, skip subsequent arithmetic processing of the neural network.

A diagnosis processing method of the present invention for diagnosing a target for abnormality by use of a neural network, and includes: a learning pattern creating step of creating a learning pattern by (i) digitalizing a learning image into digital data, the learning image being an image in which abnormality information indicating a substantive feature of abnormality of the target is pre-known, and (ii) sampling data from the digital data of the learning image by use of a predetermined sampling method, the learning pattern indicating a data sequence of a sample data row of the data thus sampled; a learning processing step of causing a neural network to learn, by using two or more learning patterns created as such in the learning pattern creating step; a diagnostic pattern creating step of creating a diagnostic pattern by (iii) digitalizing a diagnostic image into digital data, the diagnostic image being an image in which abnormality information is unknown, and (iv) sampling data from the digital data of the diagnostic image by use of the predetermined sampling method, the diagnostic pattern indicating a data sequence of a sampling data row of the data thus sampled; and a determining step of determining a substantive feature of abnormality of the target indicated in the abnormality information in the diagnostic image, based on an output value outputted, in response to an input of the diagnostic pattern, from a learned neural network which is the neural network subjected to the learning in the learning processing step.

The diagnosis processing method uses, as the learning image, the diagnostic image in which the abnormality information indicating the substantive feature of the abnormality of the diagnosis target is pre-known by a user, and digitalizes the learning image into the digital data. Then, the diagnosis processing method samples data from the digital data of the learning image by use of the predetermined sampling method. For example, data of one longitudinal pixel row of the learning image are sampled. Then, the diagnosis processing method creates the learning pattern from the data thus sampled.

Then, the diagnosis processing method causes the neural network to learn, by using the two or more learning patterns. This causes the neural network to become the learned neural network.

Then, the diagnosis processing method digitalizes the diagnostic image, in which the abnormality information is unknown by the user, into the digital data and samples the data from the digital data of the diagnostic image by use of the sampling method same as the sampling method used for creating the learning pattern. Then, the diagnosis processing method creates the diagnostic pattern from the data thus sampled.

After the input of the diagnostic pattern to the learned neural network causes the output of the output value, the diagnosis processing method determines, based on the output value of the learned neural network, the substantive feature of the abnormality of the diagnosis target indicated in the abnormality information in the diagnostic image, and then gives a result of determining to the user.

In this way, the diagnosis processing method can digitalize the diagnostic image into the digital data, sample the data from the digital data of the diagnostic image and create the diagnostic pattern from the data thus sampled, and determine the substantive feature of the abnormality of the diagnosis target indicated in the abnormality information, by using the diagnostic pattern.

This eliminates the need for an arrangement which is conventionally required for extracting of a suspicious region of interest from a diagnostic image in advance. As such, it is possible to determine the substantive feature of the abnormality of the diagnosis target indicated in the abnormality information, by using a simpler arrangement. Also, conventionally, in order to extract the suspicious region of interest from the diagnostic image, it is necessary to collect entire data in the diagnostic image and use such large amount of the data. This gives a rise to a problem that load of arithmetic processing is heavy.

In contrast, in the diagnosis processing device, it is not necessary to use the entire data. As such, it is possible to attain a great decrease in load of arithmetic processing. This is because, in the diagnosis processing device, it is possible to (i) create, for example, two or more patterns made up of respective two or more data rows sampled from the digital data of the diagnostic image, (ii) carry out arithmetic processing one after another by using the two or more patterns thus created, and (iii), when the abnormality of the diagnosis target is detected, skip subsequent arithmetic processing.

A classification processing device of the present invention is a classification processing device for classifying images to two or more groups in accordance with their patterns by use of a neural network, and includes: learning pattern creating means for creating a learning pattern by (i) digitalizing a learning image into digital data, the learning image being an image in which pattern information indicating a substantive feature of a pattern of the image is pre-known, and (ii) sampling data from the digital data of the learning image by use of a predetermined sampling method, the learning pattern indicating a data sequence of a sample data row of the data thus sampled; learning processing means for causing the neural network to learn, by use of two or more learning patterns created as above by the learning pattern creating means; classification pattern creating means for creating a classification pattern by (iii) digitalizing a classification image into digital data, the classification image being an image in which pattern information is unknown, and (iv) sampling data from the digital data of the classification image by use of the predetermined sampling method, the classification pattern indicating a data sequence of a sample data row of the data thus sampled; determining means for determining a substantive feature of the pattern indicated in the pattern information in the classification image, based on an output value outputted, in response to an input of the classification pattern, from a learned neural network which is the neural network subjected to the learning; and classifying means for classifying the classification image to any of the two or more groups, based on a result of determining by the determining means.

In the classification processing device, the learning pattern creating means uses, as the learning image, the classification image in which the patter information indicating the substantive feature of the pattern obtained from the classification image is pre-known by a user, and digitalizes the learning image into the digital data. Then, the learning pattern creating means samples the data from the digital data of the learning image by use of the predetermined sampling method. For example, data of one longitudinal pixel row of the learning image are sampled. Then, the learning pattern creating means creates the learning pattern from the data thus sampled.

The learning processing means causes the neural network to learn, by using the two or more learning patterns created by the learning pattern creating means. This causes the neural network to become the learned neural network.

The classification pattern creating means digitalizes the classification image, in which the pattern information is unknown by the user, into the digital data and samples the data from the digital data of the classification image by use of the sampling method same as the sampling method used by the learning pattern creating means. The classification pattern creating means creates the classification pattern from the data thus sampled.

After an input of the classification pattern thus created to the learned neural network causes an output of an output value, the determining means determines, based on the output value, the substantive feature of the pattern indicated in the pattern information, and outputs a result of determining to the classifying means.

In response, the classifying means classifies the image to any of the two or more groups, based on the result of determining thus received.

In this way, the classification processing device can digitalize the classification image into the digital data, sample the data from the digital data of the classification image and create the classification pattern from the data thus sampled, and determine the substantive feature of the classification pattern indicated in the pattern information in the classification information.

Further, the classification processing device can attain a great decrease in load of the arithmetic processing of the neural network. This is because the classification processing device can cause arithmetic processing of the neural network by using the data sampled from the classification image, stop the arithmetic processing after outcomes sufficient for decision making are obtained, and skip subsequent arithmetic processing.

As early described, a diagnosis processing device of the present invention includes: learning pattern creating means for creating a learning pattern from a learning image, by (i) digitalizing the learning image into digital data, and (ii) sampling data from the digital data of the learning image by use of a predetermined sampling method, wherein the learning pattern indicates a data sequence of a sample data row of the data thus sampled, and the learning image is an image in which abnormality information indicating a substantive feature of the abnormality of the target is pre-known; learning processing means for causing the neural network to learn, by use of two or more learning patterns created as above by the learning pattern creating means; diagnostic pattern creating means for creating a diagnostic pattern from a diagnostic image, by (iii) digitalizing the diagnostic image into digital data, and (iv) sampling data from the digital data of the diagnostic image by use of the predetermined sampling method, wherein the diagnostic pattern indicates a data sequence of a sample data row of the data thus sampled, and the diagnostic image is an image in which abnormality information is unknown; and determining means for determining a substantive feature of the abnormality of the target indicated in the abnormality information in the diagnostic image, based on an output value outputted, in response to an input of the diagnostic pattern, from a learned neural network which is the neural network subjected to learning.

This makes it possible to realize diagnosis by use of a simple arrangement.

DETAILED DESCRIPTION OF THE INVENTION

Embodiment 1

One embodiment of the present invention is described below with reference to FIGS. 1 through 13. A diagnosis processing device 1 is exemplified here as one example of a diagnosis processing device of Embodiment 1. In the diagnosis processing device 1, a neural network 17 is used to check, based on a chest radiograph, whether or not a lung (a diagnosis target) has abnormality such as a lung nodule or the like. The diagnosis processing device 1 of Embodiment 1 can be widely realized as a diagnosis processing device in which a neural network is used to check a substantive feature of abnormality in a human body part other than a chest, such as whether the abnormality is caused or not, a name of a disease causing the abnormality, and the like. For example, the diagnosis processing device 1 of Embodiment 1 can be realized as a diagnosis processing device in which a neural network is used to check, based on a breast radiograph, whether or not a breast (a diagnosis target) has abnormality such as a calcified-substance and/or the like.

(Arrangement of Neural Network 17)

Figure 5:
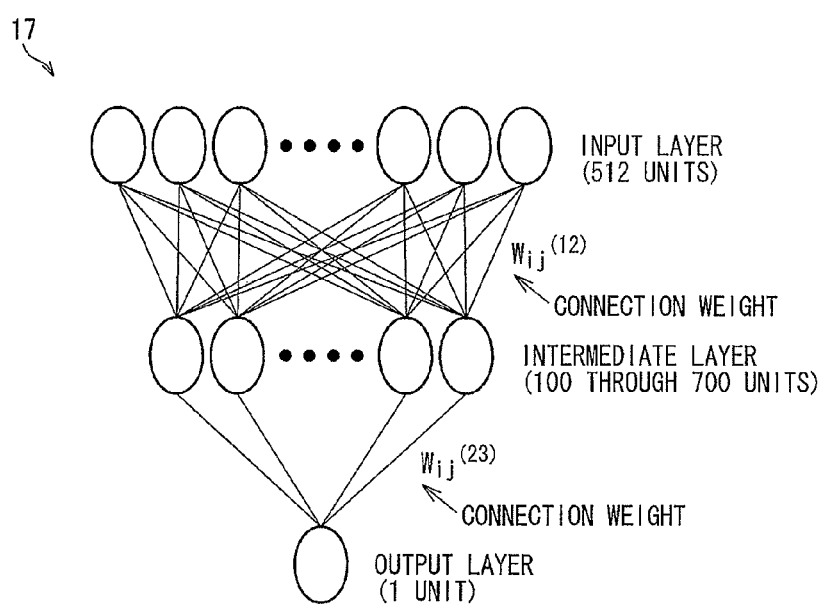
FIG. 5 is a view schematically showing an arrangement of a neural network used by the diagnosis processing device.

In the diagnosis processing device 1, the neural network 17 is used to check, based on a chest radiograph, whether a lung (diagnosis target) has abnormality or not. The neural network 17 includes three layers. FIG. 5 schematically shows an arrangement of the neural network 17.

In the neural network 17, an input layer, an intermediate layer, and an output layer are connected in this order in a direction from an input layer side toward an output layer side (see FIG. 5). Neural network 17's learning is to weight connections between the input layer and the intermediate layer and connections between the intermediate layer and the output layer, so as to have connection weights (for example, $Wij^{(12)}$) and $Wij^{(23)}$), respectively). By using the connection weights, an output of a desired output value from the output layer is made in response to an input of a given input value to the input layer.

The input layer includes 512 units. The number of the units of the input layer corresponds to the number of data that are inputted to the input layer. That is, in a case where a right lung part is targeted as a diagnosis target to be diagnosed in a chest radiograph, for example, the number of units of the input layer corresponds to the number of pieces of data in each sample data row in a learning pattern or a diagnostic pattern (which are later described) created by sampling from luminance information of each pixel constituting a right lung part image in the chest radiograph.

In reality, as later described, the sample data rows which serve as the respective learning and diagnostic patterns are sample data rows whose entire data are subjected to Fourier transform. It follows that the number of pieces of luminance information sampled from the luminance information of each pixel of the right lung part image is 512×2=1024.

If the number of pieces of original data contained in a region, data sampling from which is to be carried out, is not 1024, then the number is adjusted to 1024 by data skipping or data interpolation. This is because it is preferable to adjust the number of pieces of original data to a power of 2, in view of execution of computation using Fourier transform (fast Fourier transform) (which is later described). The sample population is not necessarily limited to 1024, because the sample population may be set as appropriate in view of the number of pieces of original data, despite that the above explanation is made on the example in which the sample population is 1024. Particularly, in a case where the number of pieces of the original data is small, it is not preferable to create data by excessive data interpolation, because such data interpolation adversely affects accuracy. In this case, networks compatible with the sampling number of 512 or 256 may be created, for example.

The intermediate layer includes about 100 to 700 units. The intermediate layer has a single-layer structure or multiple-layer structure. An output value of a unit of a higher-level layer is inputted to each of the units of the intermediate layer. In response, each of the units of the intermediate layer (i) processes the output value thus received, and (ii) outputs a result of processing of the output value to a unit of a lower-level layer, in accordance with a known neuronal function.

The output layer includes one unit. The unit of the output layer outputs an output value of a numeric range of "0" to "1". In a case where what is to be determined in response to information inputted to the input layer is whether the right lung part (diagnosis target) has the abnormality or not, the output value of the unit of the output layer indicates a probability as to whether the right lung part has the abnormality or not. For example, an output value closer to "0" indicates a higher probability that the right lung part has the abnormality, whereas an output value closer to "1" indicates a higher probability that the right lung part has no abnormality.

In the neural network 17, the units of the input layer are thus connected only with the units of the intermediate layer, and the unit of the output layer is thus connected only with the units of the intermediate layer. The connections between the units of the respective input and intermediate layers thus have the connection weights ($Wij^{(12)}$), and the connections between the units of the respective intermediate and output layers thus have the connection weights ($Wij^{(23)}$). Each of the units of the intermediate layer is connected with the entire units of the input layer, and the unit of the output layer is connected with the entire units of the intermediate layer.

The following outlines the neural network 17's learning.

Generally, a neural network before learning is no use to cause an output of a desired output value from a unit of an output layer in response to an input of data to an input layer. As such, it is necessary to cause neural network's learning in which connection weights between units are adjusted so that the input of the data to the input layer causes the output of the desired output value from the unit of the output layer.

In the present embodiment, a back propagation algorithm can be used in neural network 17's learning. During a process of the neural network 17's learning, the connection weights between the units are repeatedly adjusted so that a difference between an actual output value and the desired output value becomes minimum. This repetitive adjusting of the connection weights of the units is carried out based on the following rule:

$$\Delta Wji(n+1)=\eta(\delta pj \times Opi)+\alpha \Delta Wji(n),$$

where $\Delta Wji(n+1)$ is an adjustment amount at $(n+1)^{th}$ weight adjustment, n is the number of times the weight adjustment is repeated, $\eta$ is a learning coefficient (here, which is set to 0.05), $\delta pj$ is a difference between a target value and an actual output value, Opi is the target value, $\alpha$ is a momentum coefficient (here, which is set to 0.05), and $Wji(n)$ is an adjustment amount at $(n)^{th}$ weight adjustment.

(Diagnosis Processing Device 1)

Figure 1:
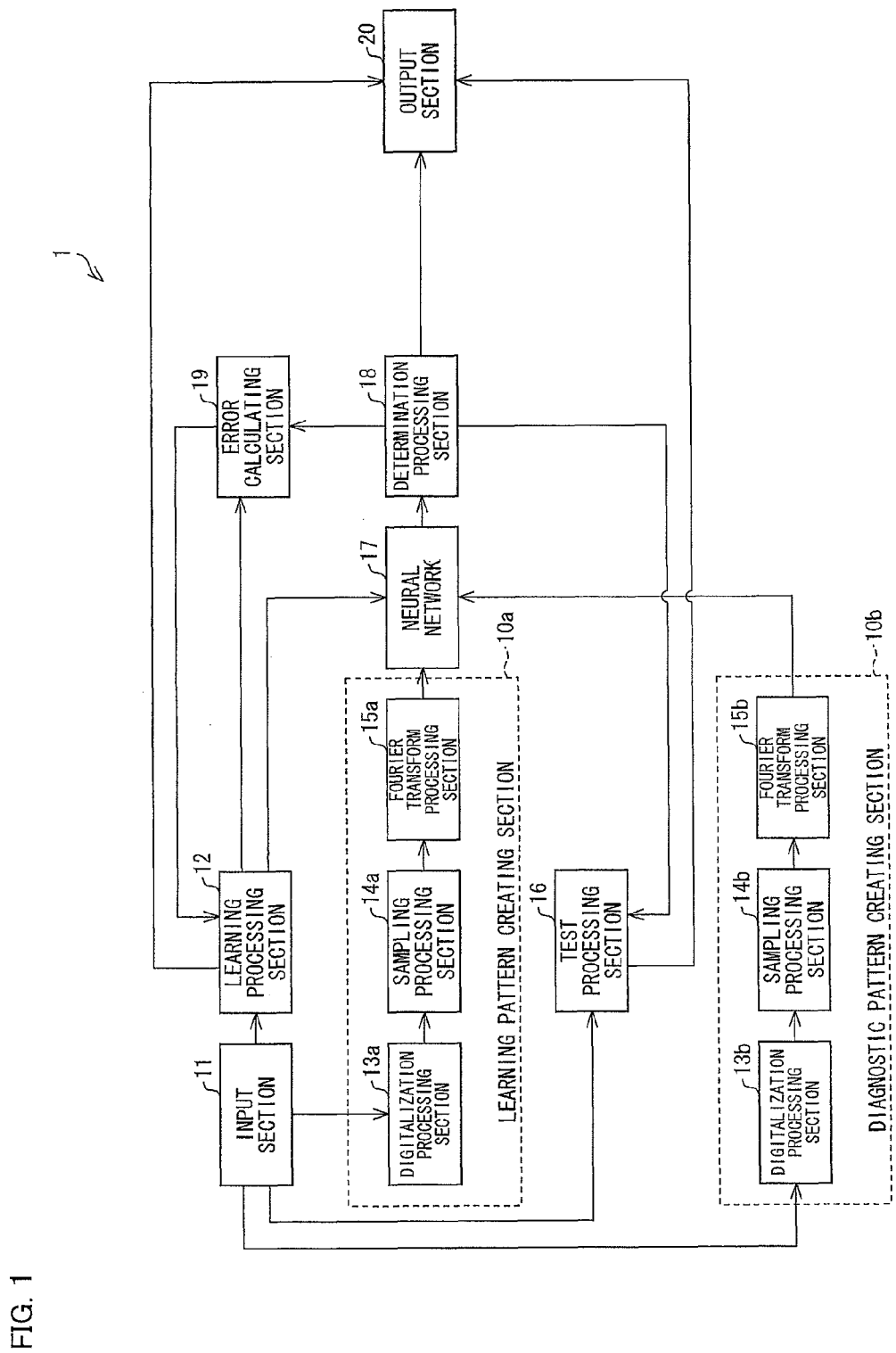
FIG. 1 is a block diagram schematically showing an arrangement of a diagnosis processing device in accordance with one embodiment of the present invention.

The diagnosis processing device 1 of the present embodiment is described below. FIG. 1 is a block diagram schematically showing the arrangement of the diagnosis processing device 1. As shown in FIG. 1, the diagnosis processing device 1 includes a learning pattern creating section (learning pattern creating means) 10a, a diagnostic pattern creating section (diagnostic pattern creating means) 10b, an input section 11, a learning processing section (learning processing means) 12, a test processing section 16, the neural network 17, a determination processing section (determining means) 18, an error calculating section (error calculating means) 19, and an output section 20.

Figure 18:
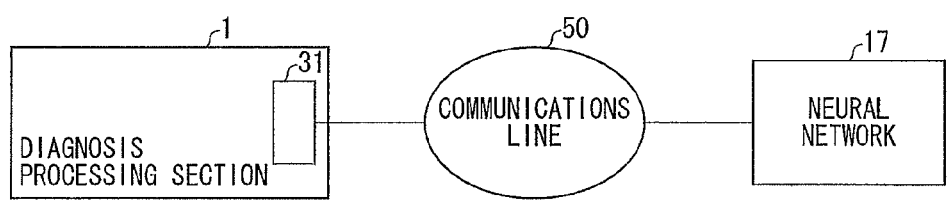
FIG. 18 is an explanation view describing a connection condition of the diagnosis processing device and the neural network.

It is not necessary that the neural network 17 is included in the diagnosis processing device 1. For example, the diagnosis processing device 1 may be connected with the neural network 17 via a known communications line 50 such as the Internet or the like, so as to be capable of sending and receiving data to/from the neural network 17 (see FIG. 18). In this case, the diagnosis processing device 1 is configured to include a communicating section (communicating means) 31 for communicating with the neural network 17 via the communications line 50.

Also, it is not necessary that the learning pattern creating section 10a and the diagnostic pattern creating section 10b be provided as two independent sections. For example, one pattern creating section, which is configured to create both the learning pattern and the diagnostic pattern (which are later described), may be used to serve as both the learning pattern creating section 10a and the diagnostic pattern creating section 10b.

Luminance information of entire pixels in a chest radiograph is inputted to the input section 11. The luminance information of entire pixels inputted to the input section 11 may be digital data subjected to digitalization in advance or analog data.

In a case where the luminance information of entire pixels inputted to the input section 11 is analog data, the luminance information of entire pixels may be read in by use of a known scanner or the like, and read-in data are organized in an electric file form (sample form, quantized form).

Then, the input section 11 outputs, to the learning pattern creating section 10a, the luminance information of entire pixels thus converted to digital data.

As later described, luminance information (i) or (ii) is inputted to the input section 11, (i) luminance information of entire pixels in a chest radiograph (learning image) in which abnormality information indicating whether a right lung part (diagnosis target) has abnormality or not is pre-known, and (ii) luminance information of entire pixels in a chest radiograph (diagnostic image) in which abnormality information indicating whether a right lung part (diagnostic target) has abnormality or not is unknown. In a case where the luminance information (i) is inputted to the input section 11, the input section 11 outputs the abnormality information in the luminance information (i) to the learning processing section 12.

The learning pattern creating section 10a includes a digitalization processing section 13a, a sampling processing section 14a, and a Fourier transform processing section 15a. In the learning pattern creating section 10a, a sampling method, which is used in creating of the learning pattern (which is later described), is set in advance.

In the sampling method, a diagnosis target region in the chest radiograph, which is a region of the diagnosis target (the right lung part), is predetermined, for example. Also, a sampling condition of data sampling from the diagnosis target region is predetermined. Examples of the sampling condition encompass a direction (sampling direction) in which data are sampled from the diagnosis target region, a width (sampling width) within which the data are sampled from the diagnosis target region, and intervals (sampling intervals) at which the data are sampled from the diagnosis target region. Sampling which is carried out in the sampling condition is sampling in which a sample population is luminance information of entire pixels in the diagnosis target region.

Provided to the learning pattern creating section 10a is such luminance information of entire pixels in the chest radiograph (learning image) that the abnormality information (abnormality presence/absence information) indicating whether the right lung part (diagnosis target) has the abnormality or not is pre-known.

The digitalization processing section 13a of the learning pattern creating section 10a obtains, from the input section 11, the luminance information of entire pixels in the chest radiograph which luminance information is digital data. Then, the digitalization processing section 13a (i) selects, from the luminance information of entire pixels, luminance information of pixels contained in the diagnosis target region predetermined by the sampling method, and (ii) reads out, as numeric data, the luminance information of the entire pixels contained in the diagnosis target region. After this, the digitalization processing section 13a outputs, to the sampling processing section 14a, the numeric data thus read out.

In response, the sampling processing section 14a of the learning pattern creating section 10a carries out, by using the numeric data thus received, data sampling in which a sample population is the luminance information of the entire pixels in the diagnosis target region. That is, the sampling processing section 14a carries out data extraction of the numeric data according to the sampling condition determined by the sampling method, and creates a sample data row.

Then, the sampling processing section 14a outputs the sample data row thus created to the Fourier transform processing section 15a.

In response, the Fourier transform processing section 15a receives the sample data row from the sampling processing section 14a. After an input of the sample data row, the Fourier transform processing section 15a carries out Fourier transformation to each data contained in the sample data row. This transforms the sample data row thus inputted to the Fourier transform processing section 15a into a power spectrum data row arranged in accordance with a frequency band pattern.

Fast Fourier transform (discrete Fourier transform) used in computation causes a second half of a data sequence of the power spectrum data row to be symmetric to a first half of the data sequence of the power spectrum data row with respect to at a middle point of the data sequence of the power spectrum data row. As such, in the fast Fourier transform, substantively, only the first half of the power spectrum data row is considered to be valid. On this account, while the number of data contained in the sample data row created by the sampling processing section 14a is 1024, the number of data contained in the power spectrum data row transformed by the Fourier transform processing section 15a is 512, i.e., a half of 1024, as early described.

Then, the Fourier transform processing section 15a outputs, to the neural network 17, the sample data row thus transformed by the Fourier transform, i.e., the power spectrum data row. In this way, a data sequence of the power spectrum data row is obtained as a learning pattern for the neural network 17 by subjecting the sample data row to the Fourier transform.

In response, the neural network 17 obtains the learning pattern from the learning pattern creating section 10a. Then, the learning of the neural network 17 is carried out as early described, by using the learning pattern.

Specifically, in the neural network 17, each of the data contained in the power spectrum data row is inputted from the learning pattern creating section 10a to a unit of the input layer. Each of the data contained in the power spectrum data row corresponds to corresponding each of the units of the input layer. Therefore, the number of the data contained in the power spectrum data row is same as the number of the units of the input layer, as early described.

In the neural network 17, an input of the data to the respective units of the input layer causes an output of an output value from the unit of the output layer, based on the current connection weights between the units of the input and intermediate layers and the current connection weights between the units of the intermediate and the output layer. The output value of the unit of the output layer is a result obtained by arithmetic processing in the neural network 17.

Then, the output value, which is the result obtained by the arithmetic processing in the neural network 17, is outputted from the neural network 17 to the determination processing section 18.

After an input of the output value from the neural network 17, the determination processing section 18 determines whether the right lung part (diagnosis target) has the abnormality or not, by using the output value thus inputted. In a case where the output value of the neural network 17 is closer to "0", the determination processing section 18 determines that there is a greater possibility that the right lung part has the abnormality. On the other hand, in a case where the output value of the neural network 17 is closer to "1", the determination processing section 18 determines that there is a greater possibility that the right lung part has no abnormality. In the present embodiment, in a case where the output value of the neural network 17 is close to "0", the determination processing section 18 determines that the right lung part has the abnormality, whereas in a case where the output value of the neural network is close to "1", the determination processing section 18 determines that the right lung part has no abnormality.

Then, the determination processing section 18 outputs a result of determining to the error calculating section 19 and the test processing section 16.

After an input of the result of determining from the determination processing section 18, the error calculating section 19 obtains, from the learning processing section 12, the abnormality information indicating whether the diagnosis target (the right lung part), for which the result of determining has been made, has the abnormality or not. Then, the error calculating section 19 calculates an error between (i) the result of determining obtained from the determination processing section 18 and (ii) the abnormality information thus obtained from the learning processing section 12.

Specifically, in a case where it is determined that the diagnosis target has the abnormality, the determination processing section 18 outputs an output value of close to "0" (in this case, the output value of close to "0" is what has been inputted from the neural network 17) to the error calculating section 19. In contrast, in a case where the it is determined that the diagnosis target has no abnormality, the determination processing section 18 outputs an output value of close to "1" (in this case, the output value of close to "1" is what has been inputted from the neural network 17) to the error calculating section 19.

On the other hand, in a case where the abnormality information indicates that the diagnosis target has the abnormality, the learning processing section 12 outputs "0" to the error calculating section 19. In contrast, in a case where the abnormality information indicates that the diagnosis target has no abnormality, the learning processing section 12 outputs "1" to the error calculating section 19.

In response, the error calculating section 19 calculates an error between (i) the value of "0" to "1" thus inputted from the determination processing section 18 and (ii) the value of "0" or "1" thus inputted from the learning processing section 12. Then, the error calculating section 19 outputs the error thus calculated to the learning processing section 12.

In response, the learning processing section 12 obtains the error calculated from the error calculating section 19. The learning processing section 12 calculates a sum of squares of errors received one after another from the error calculating section 19, and adjusts the connection weights between the units of the input and intermediate layers and the intermediate and output layers of the neural network 17 so that the sum of squares of errors becomes smaller than a predetermined threshold value, that is, the sum of squares of errors is restored. In the present embodiment, the predetermined threshold value is set to 0.001.

In this way, the learning processing section 12 can cause the neural network 17's learning.

Then, after the sum of squares of errors inputted one after another from the error calculating section 19 becomes smaller than the threshold value, the learning processing section 12 reports to the output section 20 that the sum of squares of errors has become smaller than the threshold value.

However, if the number of times of the neural network 17's learning reaches a predetermined number before the sum of squares of errors becomes smaller than the predetermined threshold value, then the learning processing section 12 can finish the neural network 17's learning.

In this case, learning patterns created by the learning pattern creating section 10a are repeatedly inputted to the neural network 17 until the sum of squares of errors becomes smaller than the predetermined threshold value or the number of times of the neural network 17's learning reaches the predetermined number.

After the neural network 17's learning, a learning pattern created by the learning pattern creating section 10a is inputted to the neural network 17 thus subjected to the learning (hereinafter, referred to as a learned neural network 17). In this way, the test processing section 16 checks, by using the learning pattern as a test pattern, whether the determination processing section 18 can make correct determination based on an output value of the learned neural network 17, or not.

Specifically, the test processing section 16 obtains abnormality information in the learning pattern from the input section 11, and checks whether or not the determination processing section 18 makes determination consistent with the abnormality information indicative of presence or absence of the abnormality. Then, the test processing section 16 outputs a result of checking to the output section 20.

The diagnostic pattern creating section 10b includes a digitalization processing section 13b, a sampling processing section 14b, and a Fourier transform processing section 15b. In the diagnostic pattern creating section 10b, a sampling method, which is same as the sampling method used by the learning pattern creating section 10a for creating the learning pattern, is preset.

Luminance information of entire pixels in a chest radiograph (diagnostic image), in which abnormality information (abnormality presence/absence information) indicating whether a right lung part (diagnosis target) has abnormality or not is unknown, is inputted to the diagnostic pattern creating section 10b.

Operations of the digitalization processing section 13b, the sampling processing section 14b, and the Fourier transform processing section 15b of the diagnostic pattern creating section 10b are same as the operations of the digitalization processing section 13a, the sampling processing section 14a, and the Fourier transform processing section 15a of the learning pattern creating section 10a, respectively. Therefore, the operations of the digitalization processing section 13b, the sampling processing section 14b, and the Fourier transform processing section 15b of the diagnostic pattern creating section 10b are not repeatedly described here.

In essence, what is different between the learning pattern creating section 10a and the diagnostic pattern creating section 10b is that the learning pattern creating section 10a receives, from the input section 11, luminance information of entire pixels in a learning image in which abnormality information indicating whether the diagnosis target has abnormality or not is pre-known, whereas the diagnostic pattern creating section 10b receives, from the input section 11, luminance information of entire pixel in a diagnostic image in which abnormality information indicating whether the diagnosis target has abnormality or not is unknown.

Results of outputs of the learning processing section 12, the test processing section 16, and the decision processing section 18 are inputted to the output section 20. In response, the output section 20 displays, to a user, the results of outputs thus received. A known display device and a known printer device can be used to serve as the output section 20.

An operation of the diagnosis processing device 1 is described below.

Figure 2:
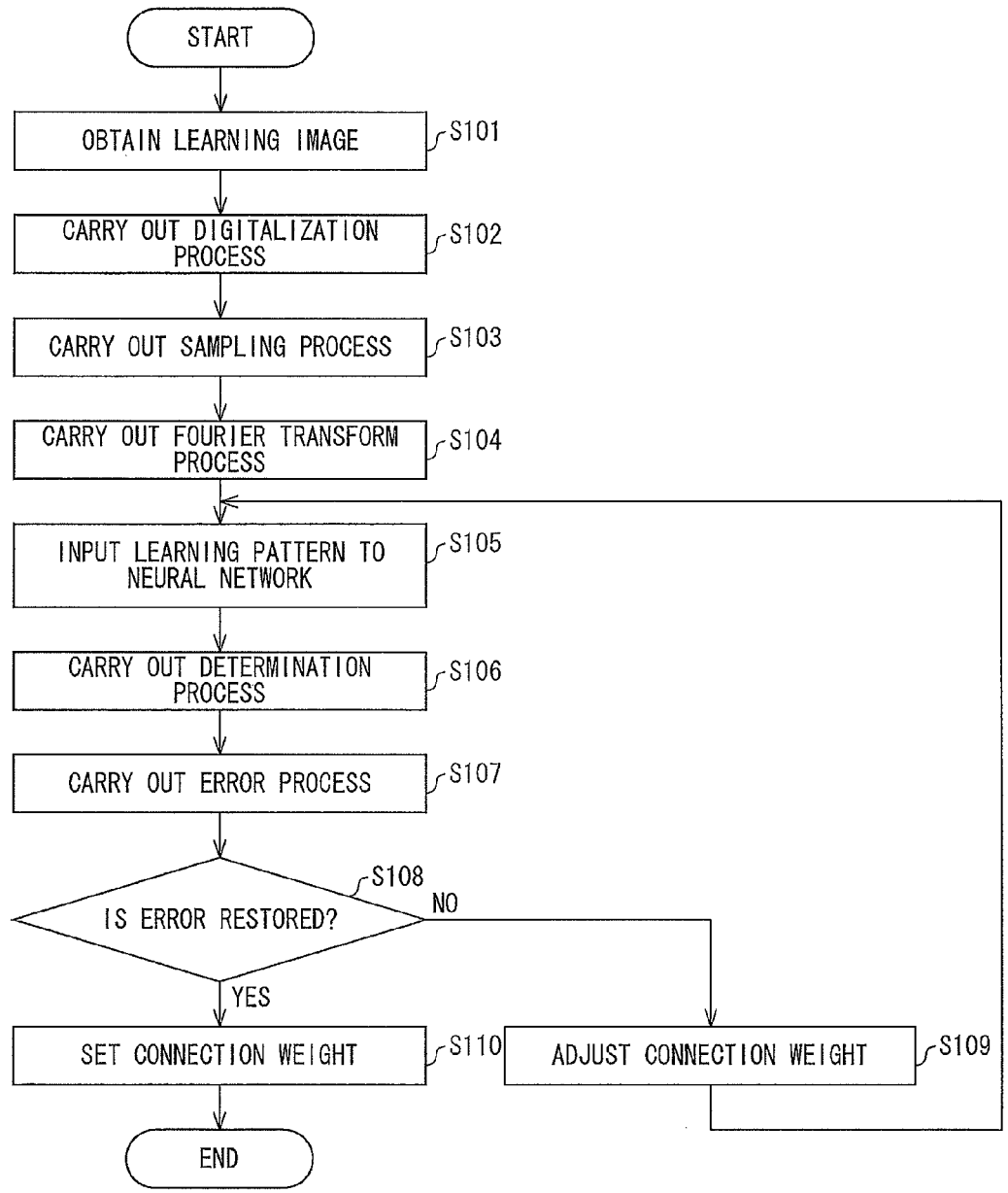
FIG. 2 is a flow chart showing a process flow of a learning operation of the diagnosis processing device.

First, a learning operation of the diagnosis processing device 1 is described. FIG. 2 is a flow chart showing a process flow of the learning operation of the diagnosis processing device 1.

The input section 11 obtains the learning image (step S101) (see FIG. 2). In the step S101, the input section 11 obtains the luminance information of entire pixels in the learning image in which the abnormality information indicating whether the diagnosis target has the abnormality or not is pre-known. Then, the input section 11 outputs the luminance information thus obtained to the digitalization processing section 13a of the learning pattern creating section 10a.

In response, the digitalization processing section 13a of the learning pattern creating section 10a carries out a digitalization process to the luminance information thus inputted from the input section 11 (step S102). In the step S102, the digitalization processing section 13a (i) selects those pixels in the learning image which are contained in the diagnosis target region determined by the sampling method, and (ii) reads out, as numeric data, luminance information of the pixels thus selected. Then, the digitalization processing section 13a outputs, to the sampling processing section 14a of the learning pattern creating section 10a, the numeric data thus read out.

In response, the sampling processing section 14a carries out a sampling process by using the numeric data thus inputted from the digitalization processing section 13a (step S103). In the step S103, the sampling processing section 14a carries out the sampling in which a sample population is the luminance information of the entire pixels in the diagnosis target region thus received from the digitalization processing section 13a. More specifically, the sampling processing section 14a carries out data extraction of the numeric data according to the sampling condition determined by the sampling method, and creates a sample data row.

Figure 6:
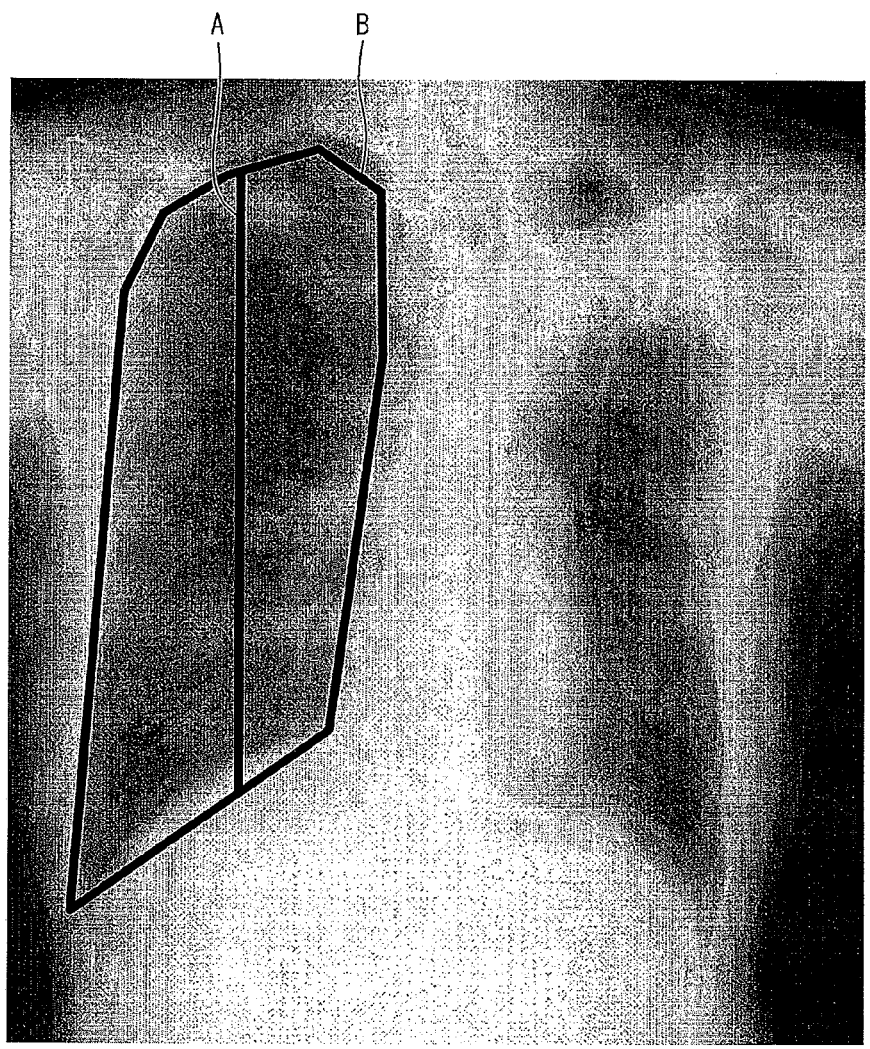
FIG. 6 is an explanation view describing a sampling method used by the diagnosis processing device.
Figure 7:
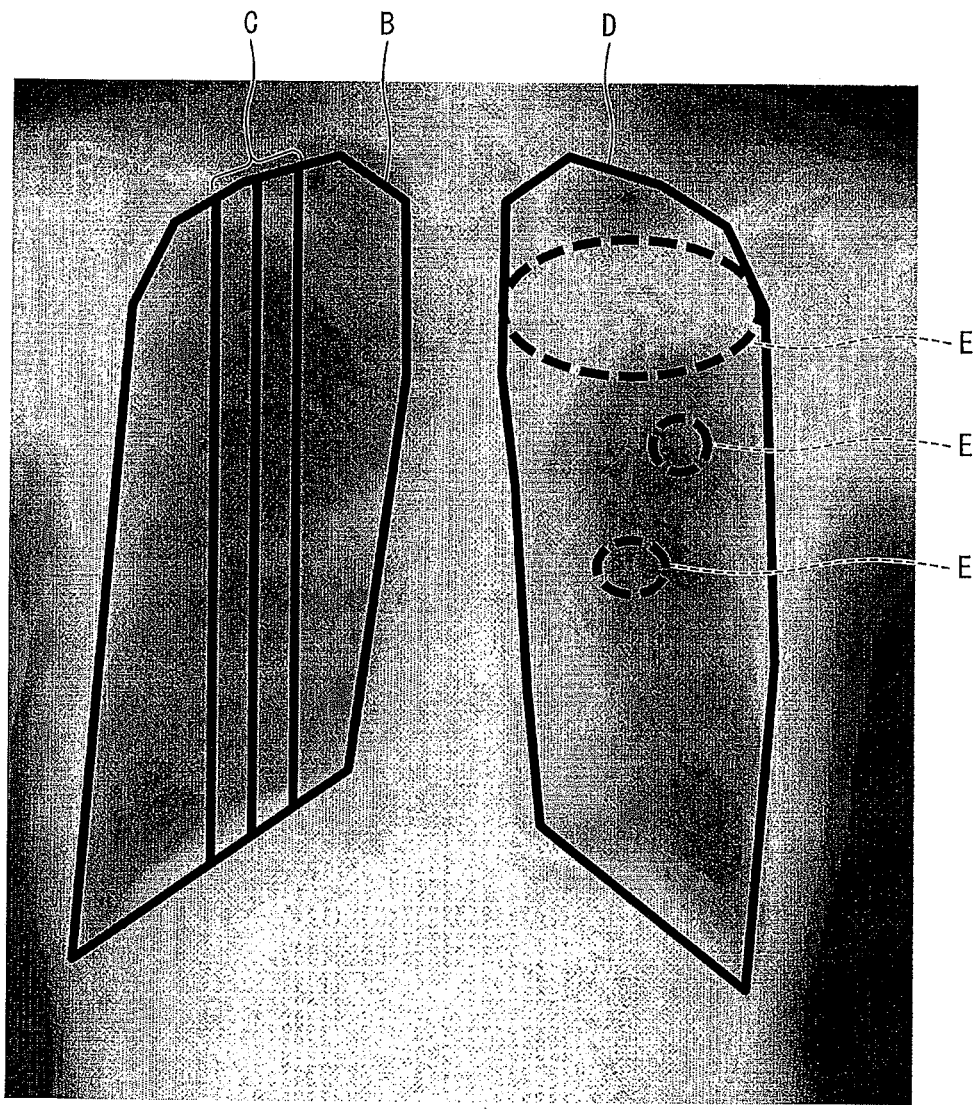
FIG. 7 is an explanation view describing a sampling method used by the diagnosis processing device.
Figure 8:
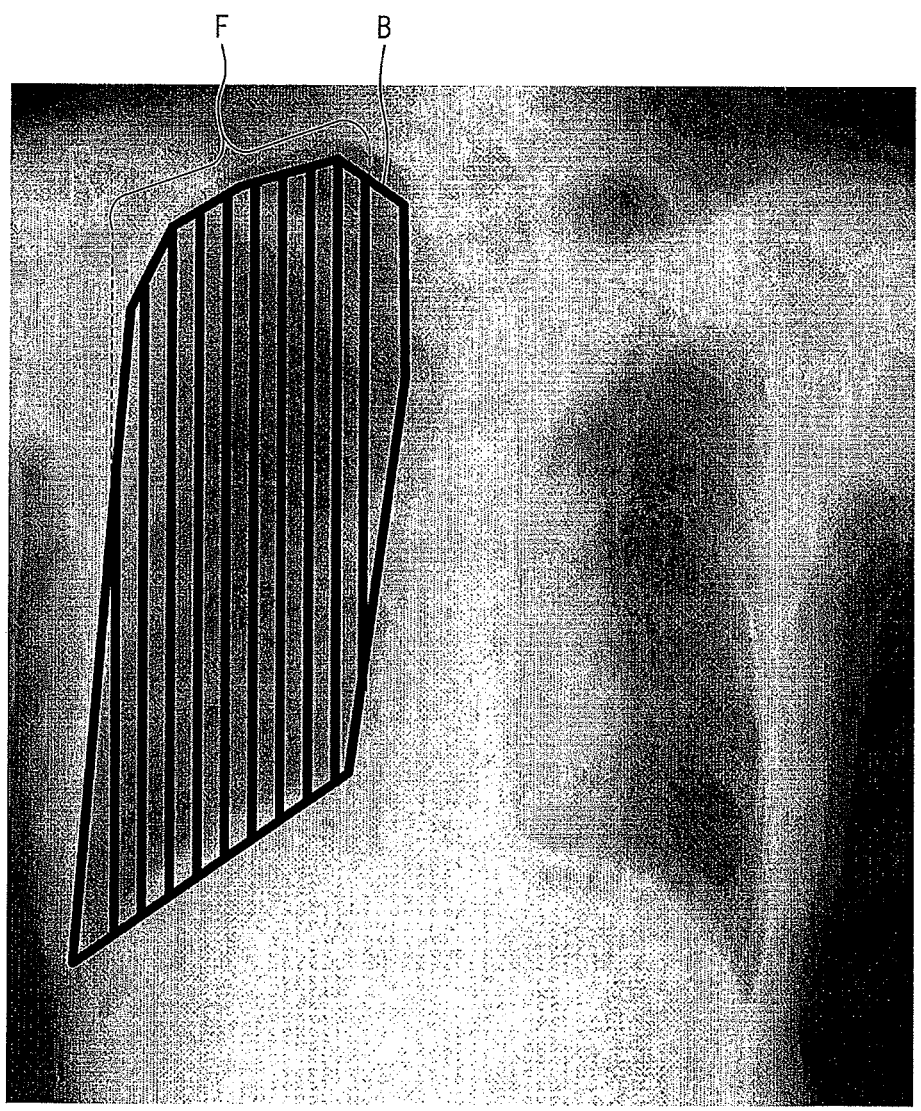
FIG. 8 is an explanation view describing a sampling method used by the diagnosis processing device.
Figure 9:
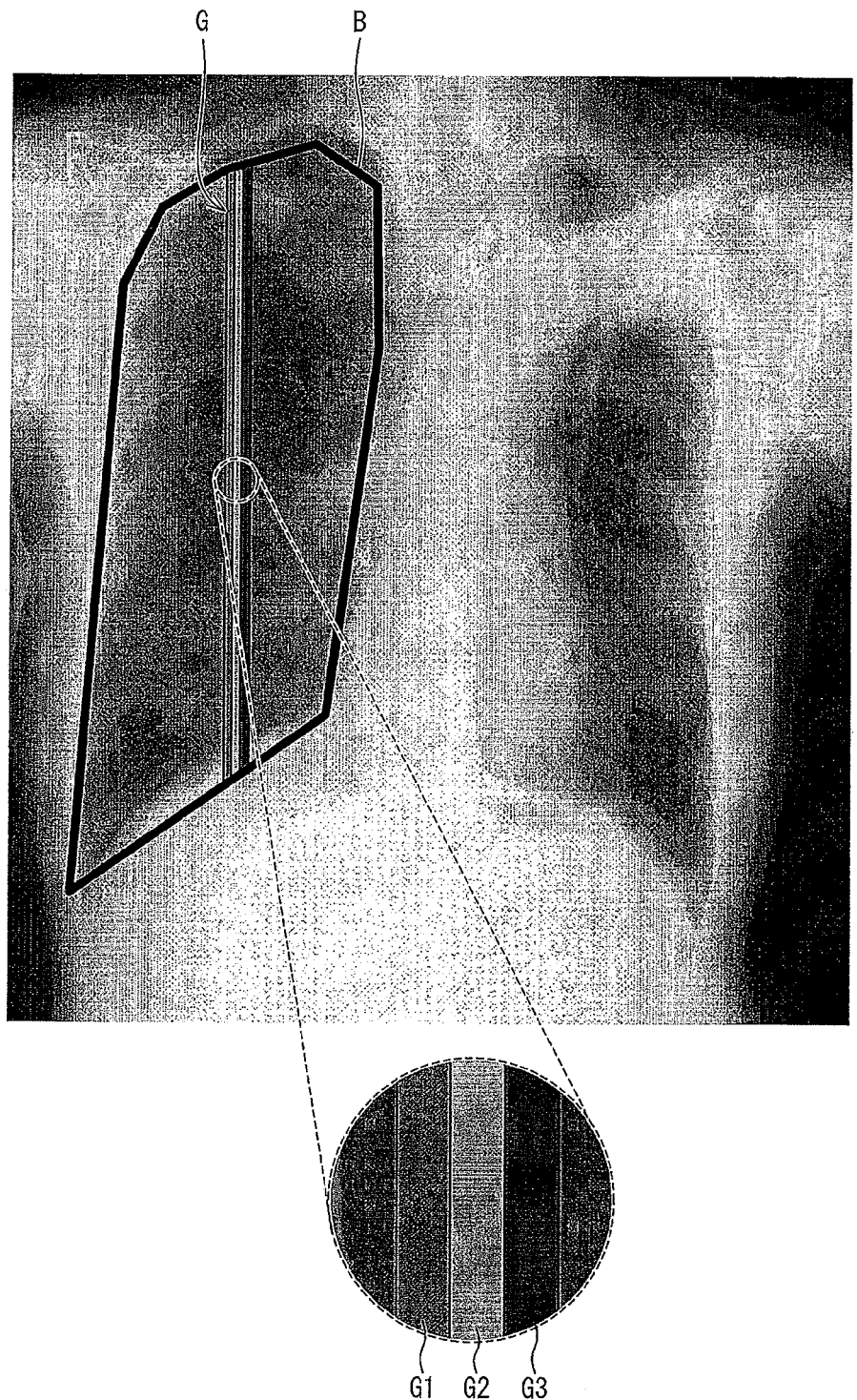
FIG. 9 is an explanation view describing a sampling method used by the diagnosis processing device.

For example, the sampling condition can be (i) one sample pattern indicated by "A" in FIG. 6, which extends in a longitudinal direction of FIG. 6 in a right lung part (diagnosis target) indicated by "B", or (ii) three sample patterns indicated by "C" in FIG. 7, which extend in a longitudinal direction of FIG. 7 in a right lung part indicated by "B", have widths of one pixel, and are arranged at intervals of 50 pixels.

The number of sample patterns obtained from a radiograph may be different between the sampling condition employed in the learning operation and the sampling condition employed in a diagnostic operation (which is later described). For example, in the learning operation, one sample pattern (see FIG. 6) or three sample patterns (see FIG. 7) as early described can be used, whereas in the diagnostic operation, more than three sample patterns as indicated by "F" in FIG. 8 can used. Further, a width of each sample pattern can be determined based on actual size measurement or dot counting. In a case where a width of each sample pattern is as wide as a combined width of a plurality of dots G1, G2, and G3 (see FIG. 9), it is possible to employ an average luminance for the dots G1, G2, and G3.

In this way, the number of the sample patterns used in the learning operation is smaller than the number of the sample patterns used in the diagnostic operation. This makes it possible to efficiently carry out the learning operation. In contrast, if a large number of sample patterns are used in the learning operation, then it is impossible to restore an error even by repeating the learning operation plural times. This gives a rise to a risk that the learning operation is not completed.

In the method of the patent literature 1 for detecting a micro-calcified substance, for example, it is necessary to (i) find regions of interest indicated by "E" in FIG. 7 from a left right lung part indicated by "D" in FIG. 7, and (ii) selectively extract the regions of interest. This requires arithmetic processing in which luminance information of entire pixels in an image of the left lung part "D" is used. As such, load of the arithmetic processing is very heavy.

In contrast, in the diagnosis processing device 1, it is only required that arithmetic processing in the neural network is carried out one after another by using two or more patterns made up of respective two or more sample data rows sampled from the luminance information of the entire pixels in the right lung part "B". Further, after the abnormality is detected by given arithmetic processing, it is possible to skip arithmetic processing subsequent to the given arithmetic processing.

Therefore, in the diagnosis processing device 1, it is not necessary to use entire data. This can attain a greater decrease in load of the arithmetic processing in the neural network 17, as compared with the conventional art.

After creating of the sample data row, the sampling processing section 14a outputs the sample data row to the Fourier transform processing section 15a of the learning pattern creating section 10a.

Figure 10:
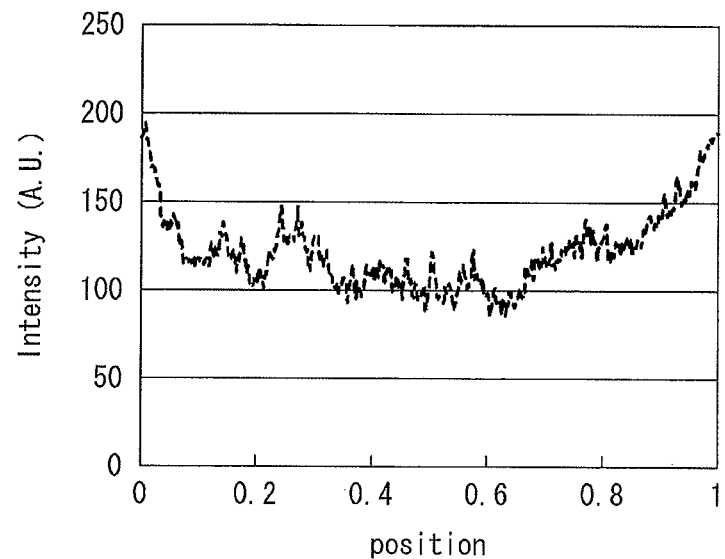
FIG. 10 is a graph showing a relationship between a sampling location and a value (intensity) of each data in a sample data row.

FIG. 10 shows numeric values of the data contained in the sample data row created by the sampling processing section 14a. In FIG. 10, the horizontal axis indicates positions of the data sampled, and the longitudinal axis indicates numeric values (intensities) of the data sampled. Here, the number of the positions of the data sampled is 1024. However, on the horizontal axis of the graph, the positions of the data sampled are shown within a range with a maximum value of "1".

After an input of the sample data row from the sampling processing section 14a, the Fourier transform processing section 15a carries out a Fourier transform process to each of the data contained in the sample data row thus inputted (step S104). In the step S104, the Fourier transform processing section 15a transforms the sample data row into the power spectrum data row arranged in accordance with the frequency band pattern. As early described, the data sequence of the power spectrum data row is used as the learning pattern.

Figure 11:
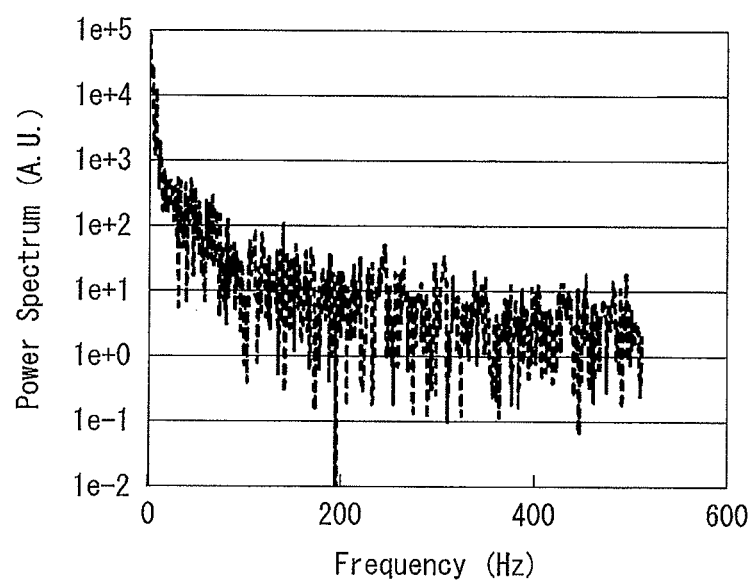
FIG. 11 is a graph showing a relationship between a frequency and an intensity power of each data in a power spectrum data row.

FIG. 11 shows an intensity power of each of data contained in the power spectrum data row thus transformed by the Fourier transform process by the Fourier transform processing section 15a. In FIG. 11, the horizontal axis indicates a frequency of the each of data, and the longitudinal axis indicates an intensity power of the each of data. A pattern of the power spectra of the data with respect to the frequencies is (i) the learning pattern created by the learning pattern creating section 10a and (ii) the diagnostic pattern created by the diagnostic pattern creating section 10b. In the present embodiment, the sample data row is transformed by the Fourier transform prior to being inputted to the neural network 17. As an alternative transform method, a generally known filter process, e.g., smoothing (median smoothing, Gaussian smoothing) and sharpening (derivative sharpening, second derivative sharpening), may be used alone or in combination with the Fourier transform process.

After transforming of the sample data row to the power spectrum data row, the Fourier transform processing section 15a outputs the power spectrum data row to the neural network 17 (step S105). In the step S105, the each of data contained in the power spectrum data row is inputted from the Fourier transform processing section 15a to a unit of the input layer of the neural network 17. This causes the output of the output value from the unit of the output layer of the neural network 17. The output value is the result obtained by the arithmetic processing in the neural network 17. Then, the output value is outputted from the neural network 17 to the determination processing section 18.

In response, the determination processing section 18 carries out, by use of the output value of the neural network 17, a determination process for determining whether the diagnosis target has the abnormality or not (step S106). In the step S106, for example, the determination processing section 18 determines that the diagnosis target has the abnormality, in a case where the output value of the neural network 17 is close to "0", and determines that the diagnosis target has no abnormality, in a case where the output value of the neural network 17 is close to "1". Then, the determination processing section 18 outputs a result of determining to the error calculating section 19.

After an input of the result of determining from the determination processing section 18, the error calculating section 19 calculates an error between (i) the result of determining thus inputted and (ii) the abnormality information, which indicates whether the diagnosis target has the abnormality or not, thus obtained from the learning processing section 12 (step S107). In the step S107, thereafter, the error calculating section 19 outputs the error thus calculated to the learning processing section 12.

After an input of the error calculated by the error calculating section 19, the learning processing section 12 determines whether the error is restored or not (step S108). In the step S108, after the input of the error thus calculated, the learning processing section 12 calculates, by use of the error and another error having been inputted prior to the error, a sum of squares of the errors between (i) the results of determining inputted one after another from the determination processing section 18 and (ii) the abnormality information obtained from the input section 11.

Then, in a case where the sum of squares of the errors is smaller than the predetermined threshold value, the learning processing section 12 determines that the errors between the results of determining inputted from the determination processing section 18 and the abnormality information obtained from the input section 11 are restored (YES in step S108). In this case, the learning processing section 12 sets the current connection weights in the neural network 17 as connection weights in the learned neural network 17 (step S110). In the step S110, the learning processing section 12 outputs, to the output section 20, a result of determining that the errors between the results of determining inputted from the determination processing section 18 and the abnormality information obtained from the input section 11 are restored.

In contrast, in a case where the sum of squares of errors is not smaller than the predetermined threshold value, the learning processing section 12 determines that the errors between (i) the results of determining inputted from the determination processing section 18 and (ii) the abnormality information obtained from the input section 11 has not been restored yet (NO in the step S108). In this case, the learning processing section 12 adjusts the connection weights in the neural network 17 (step S109). In the step S109, the learning processing section 12 may output, to the output section 20, a result of determining that the errors between (i) the results of determining thus inputted and (ii) the abnormality information thus obtained has not been restored yet.

If the predetermined threshold value is set to a great value, then it is possible to finish the learning operation of the neural network 17 early. In contrast, if the predetermined threshold value is set to a small value, then it is possible to increase an effect of the neural network 17's learning.

An optimized value of the predetermined threshold value may be determined specifically by (i) carrying out learning operations by use of respective different threshold values, (ii) working out false acceptance rates (error rates of erroneously determining that the diagnosis target has no abnormality) and false rejection rates (error rates of erroneously determining that the diagnosis target has abnormality), and (iii) carrying out comparison of the false acceptance rates and comparison of the false rejection rates.

Thereafter, the learning operation is returned to the step S105 so that a next learning pattern is created by the learning pattern creating section 10a and inputted to the neural network 17 (the step S105).

As early described, after the number of times of the neural network 17's learning reaches the predetermined number, the learning processing section 12 sets the current connection weights in the neural network 17 as the connection weights in the learned neural network 17 (the step S110), even if it is determined that there are still errors between the results of determining inputted from the determination processing section 18 and the abnormality information obtained from the input section 11.

In this way, the learning operation of the diagnosis processing device 1 is finished.

Figure 12:
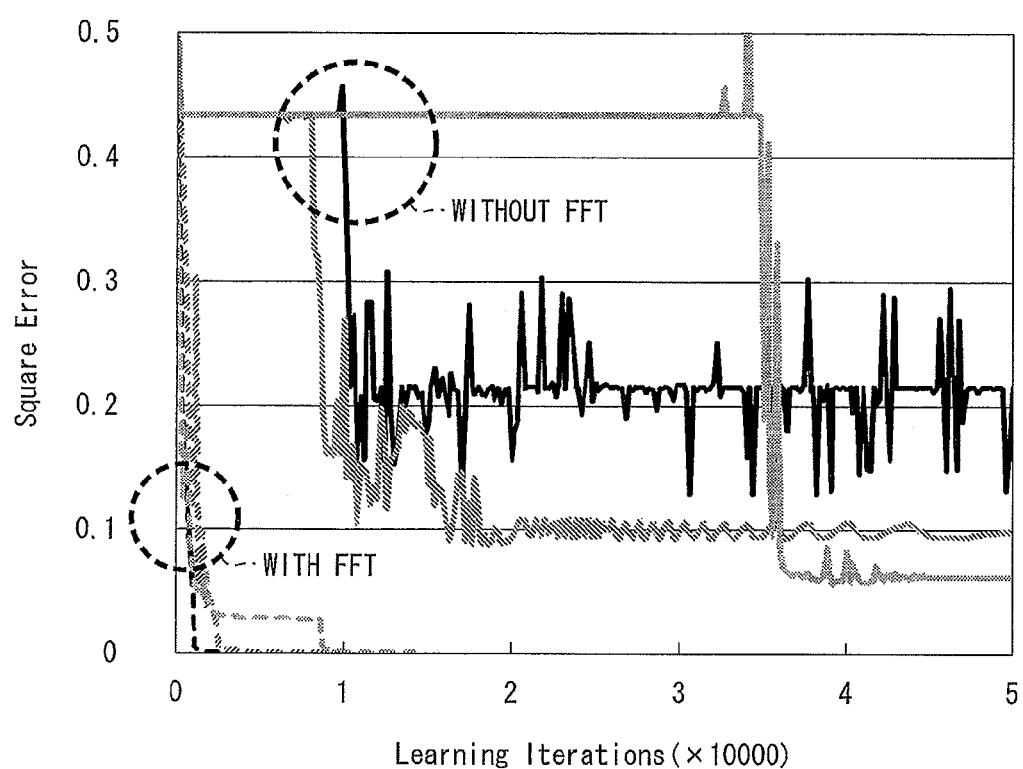
FIG. 12 is a graph showing a relationship between the number of times of neural network's learning and an error sum of squares of output values of the neural network.

FIG. 12 shows a relationship between the number of times of the neural network 17's learning and the sum of squares of errors calculated by the learning processing section 12. A horizontal axis in FIG. 12 indicates the number of times of the neural network 17's learning (Learning Iterations) in which the learning pattern created by the learning patterns creating section 10a are used. A longitudinal axis in FIG. 12 indicates the sum of squares of errors (Square Error) calculated, by the learning processing section 12, by use of the errors calculated by the error calculating section 19. Three graphs indicated by "with FFT" in FIG. 12 correspond to relationships each obtained in a case where the neural network 17 learns with the use of the power spectrum data row transformed by the Fourier transform processing section 15a (here, this case is referred to as "a case with Fourier transform"). Three graphs indicated by "without FFT" in FIG. 12 correspond to relationships each obtained in a case where the neural network 17 learns with the use of the sample data row created by the sampling processing section 14a but not subjected to the Fourier transform (here, this case is referred to as "a case with no Fourier transform").

Learning of the neural network 17 by using learning patterns with Fourier transform was carried out by three times. After about $10,000^{th}$ neural network 17's learning, the sums of squares of errors became smaller than the threshold value as illustrated in FIG. 12. That is, the neural network 17's learning performed by the learning processing section 12 reached restoration as illustrated in FIG. 12.

On the other hand, learning of the neural network 17 by using learning patterns without Fourier transform was carried out by three times. The results showed that there was a tendency that the sums of squares of errors were restored by increasing the number of times of the neural network 17's learning. However, the result shown in FIG. 12 clearly demonstrates that the time required for attaining the restoration in the errors was longer, that is, the number of times of the neural network 17's learning was larger, as compared with the cases with Fourier transform.

As such, from a perspective of attaining a decrease in the number of times of the neural network 17's learning, it is more preferable to cause the neural network 17 to learn, by using the power spectrum data row transformed by the Fourier transform processing section 15a.

Figure 13:
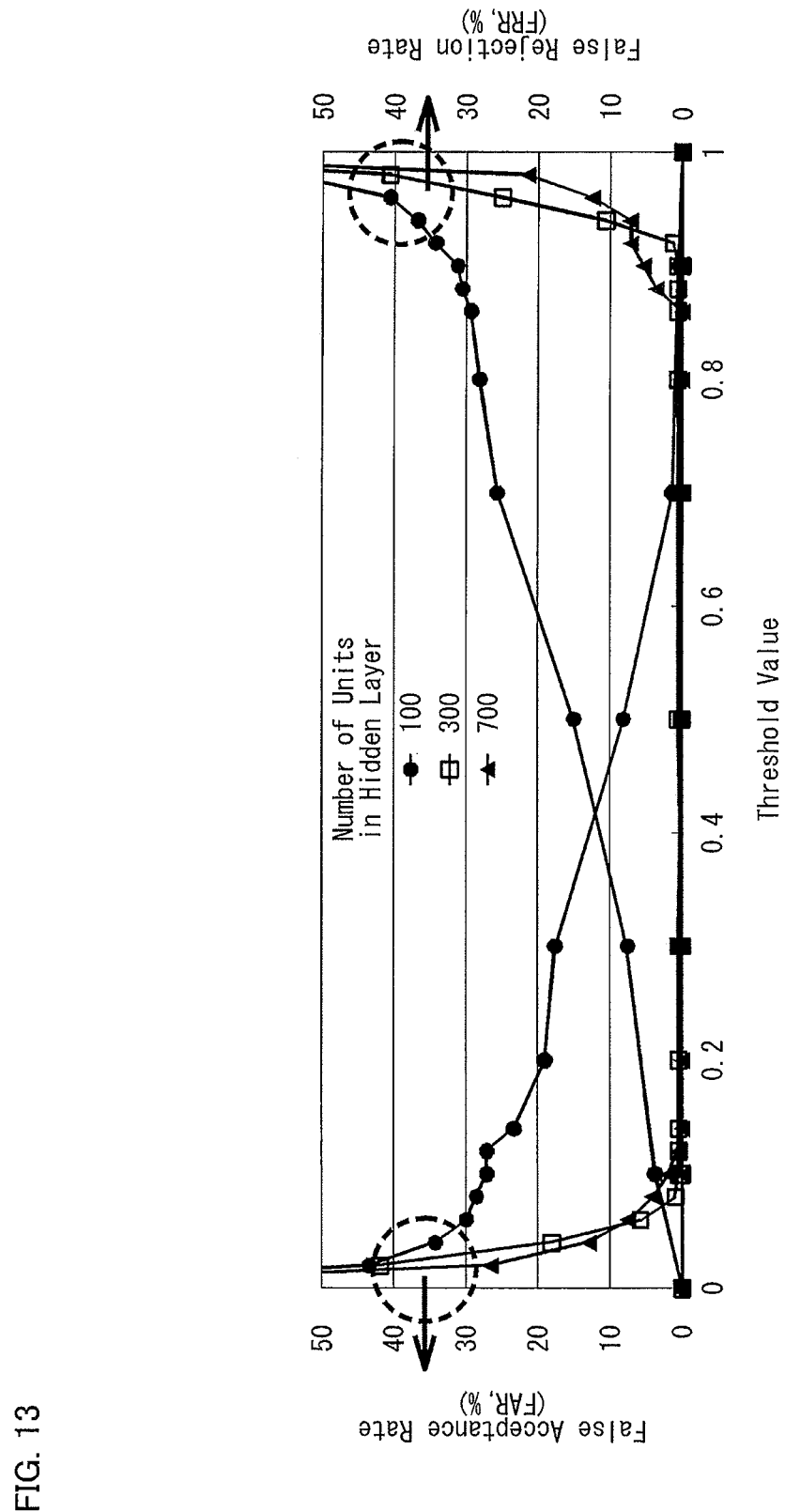
FIG. 13 is a graph showing a relationship between (i) a threshold value in a determination process and (ii) error rates of false acceptance and false rejection of abnormality in a result of the determination process.

FIG. 13 shows a relationship between (i) a threshold in a determination process of the determination processing section 18 and (ii) error rates of results of determining made by the determining section 18, i.e., a false acceptance rate (an error rate of erroneously determining that there is no abnormality) and a false rejection rate (an error rate of erroneously determining that there is abnormality).

The threshold value in the determination process of the determination processing section 18 is as follows.

As early described, in a case where the output value of the neural network 17 is close to "0", the determination processing section 18 determines that the diagnostic target has the abnormality, whereas in a case where the output value of the neural network 17 is close to "1", then the determination processing section 18 determines that the diagnostic target has no abnormality. In the determination process, in practice, whether the output value of the neural network 17 is close to "0" or "1" is determined based on the threshold value which is set in a range of "0" to "1".

In FIG. 13, the number of the units of the intermediate layer (Hidden Layer) of the neural network is set to 100, 300, and 700.

As is clear from FIG. 13, in a case where the units of the intermediate layer of the neural network 17 is set to 100, an error rate of false acceptance of the abnormality and an error rate of false rejection of the abnormality are 10% or higher at their intersection. As such, it cannot be said that the determination processing section 18 has made a correct decision.

On the other hand, in a case where the number of the units of the intermediate layer is set to 300 and 700, both of the error rates are zero in a broad range of the threshold value. As such, it can be said that the determination processing section 18 has made a correct decision.

In view, it is preferable that the number of the units of the intermediate layer of the neural network 17 is set to 300 or greater.

Increasing of the number of the units of the intermediate layer attains improvement in performance of the neural network. However, if the number of the units of the intermediate layer is increased to reach a certain number, then further increasing of the number of the units of the intermediate layer does not cause further improvement in the performance of the neural network 17. Generally, it is preferable that an upper limit of the number of the units of the intermediate layer is about two times greater than the number of the units of the input layer.

Figure 3:
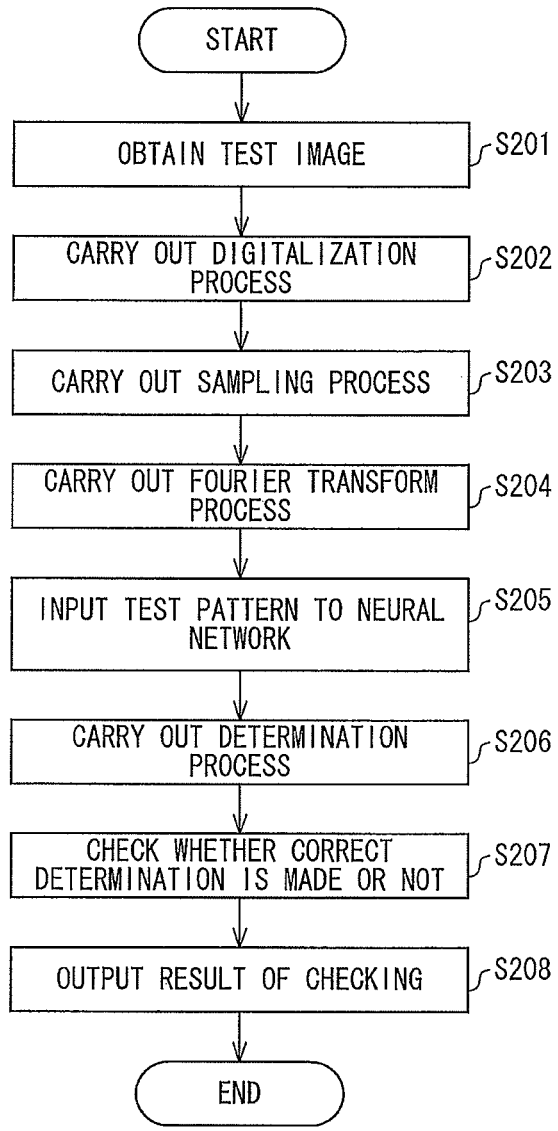
FIG. 3 is a flow chart showing a process flow of a test operation of the diagnosis processing device.

A test operation of the diagnosis processing device 1 is described below. FIG. 3 is a flow chart showing a process flow of the test operation of the diagnosis processing device 1.

The input section 11 obtains a learning image used as a test image (step S201) (see FIG. 3). In the step S201, the input section 11 obtains luminance information of entire pixels in the test image in which the abnormality information indicating whether a diagnosis target has abnormality or not is pre-known. Then, the input section 11 outputs the luminance information of entire pixels thus obtained to the digitalization processing section 13a of the learning pattern creating section 10a.

In response, the digitalization processing section 13a of the learning pattern creating section 10a carries out a digitalization process to the luminance information of entire pixels in the test image thus inputted from the input section 11 (step S202). In the step S202, the digitalization processing section 13a (i) selects those pixels in the test image which are contained in a diagnosis target region determined by the sampling method, and (ii) reads out, as numeric data, luminance information of the pixels thus selected. Then, the digitalization processing section 13a outputs, to the sampling processing section 14a of the learning pattern creating section 10a, the numeric data thus read out.

In response, the sampling processing section 14a carries out a sampling process by using the numeric data inputted from the digitalization processing section 13a (step S203). In the step S203, the sampling processing section 14a carries out sampling in which a sample population is the luminance information of the entire pixels in the diagnostic target region received from the digitalization processing section 13a. More specifically, the sampling processing section 14a carries out data extraction of the numeric data according to the sampling condition determined by the sampling method, and creates a sample data row. Then, the sampling processing section 14a outputs the sampling data row thus created to the Fourier transform processing section 15 of the learning pattern creating section 10a.

In response, the Fourier transform processing section 15a carries out a Fourier transform process to each of data contained in the sampling data row received from the sampling processing section 14a (step S204). That is, in the step S204, the Fourier transform processing section 15a transforms the sampling data row to a power spectrum data row arranged based on a frequency band pattern. A data sequence of the power spectrum data row is used to serve as the test pattern.

Then, the Fourier transform processing section 15a outputs, to the neural network 17, the power spectrum data row thus transformed (step S205). In the step S205, each of data contained in the power spectrum data row is inputted from the Fourier transform processing section 15a to a unit of the input layer of the neural network 17. This causes an output of an output value from the unit of the output layer of the neural network 17. The output value thus outputted is a result obtained by arithmetic processing of the neural network 17. Then, the output value is outputted from the neural network 17 to the determination processing section 18.

In response, the determination processing section 18 carries out, by using the output value of the neural network 17, a determination process for determining whether the diagnosis target has abnormality or not (step S206). In the step S206, for example, the determination processing section 18 determines that the diagnosis target has abnormality, in a case where the output value of the neural network 17 is close to "0", and determines that the diagnosis target has no abnormality, in a case where the output value of the neural network 17 is close to "1". Then, the determination processing section 18 outputs a result of determining to the test processing section 16.

In response, the test processing section 16 checks whether the result of determining inputted from the determination processing section 18 is correct or not (step S207). Specifically, in the step S207, after an input of the result of determining from the determination processing section 18, the test processing section 16 checks whether the result of determining is correct or not, by comparing the result of determining with the abnormality information obtained from the input section 11.

Then, the test processing section 16 outputs a result of checking to the output section 20 (step S208).

In this way, the test operation of the diagnosis processing device 1 is finished.

Figure 4:
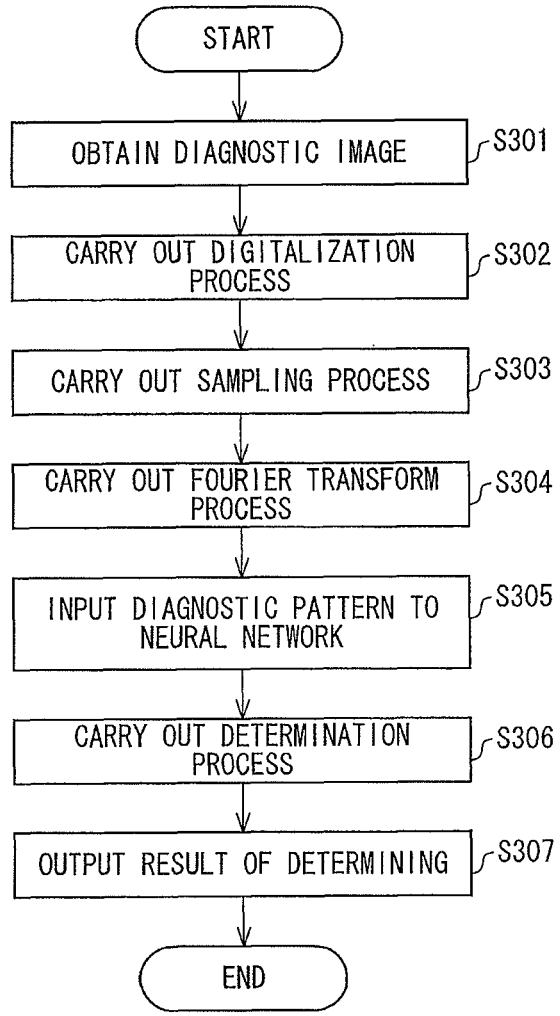
FIG. 4 is a flow chart showing a process flow of a diagnosis operation of the diagnosis processing device.

A diagnostic operation of the diagnosis processing device 1 is described below. FIG. 4 is a flow chart showing a process flow of the diagnostic operation of the diagnosis processing device 1.

The input section 11 obtains a diagnostic image (step S301) (see FIG. 4). Specifically, in the step S301, the input section 11 obtains luminance information of entire pixels in that diagnostic image in which abnormality information indicating whether a diagnosis target has abnormality or not is unknown. Then, the input section 11 outputs the luminance information thus obtained to the digitalization processing section 13b of the diagnostic pattern creating section 10b.

After that, the digitalization processing section 13b of the diagnostic pattern creating section 10b carries out a digitalization process to the luminance information inputted from input section 11 (step S302). Specifically, in the step S302, the digitalization processing section 13b (i) selects those pixels in the diagnostic image which are contained in a diagnosis target region determined by a sampling method same as the sampling method used by the learning pattern creating section 10a, and (ii) reads out, as numeric data, luminance information of the pixels thus selected. Then, the digitalization processing section 13b outputs, to the sampling processing section 14b of the diagnostic pattern creating section 10b, the numeric data thus read out.

After that, the sampling processing section 14b carries out a sampling process by using the numeric data inputted from the digitalization processing section 13b (step S303). That is, in the step S303, the sampling processing section 14b carries out sampling in which a sample population is luminance information of the entire pixels in the diagnosis target region thus received from the digitalization processing section 13b. More specifically, the sampling processing section 14b carries out data extraction of the numeric data according to a sampling condition determined by the sampling method, and creates a sample data row. Thereafter, the sampling processing section 14b outputs the sample data row thus created to the Fourier transform processing section 15b of the diagnostic pattern creating section 10b.

After that, the Fourier transform processing section 15b carries out a Fourier transform process to each of the data contained in the sampling data row received from the sampling processing section 14b (step S304). Specifically, in the step S304, the Fourier transform processing section 15b transforms the sampling data row to a power spectrum data row arranged based on a frequency band pattern. A data sequence of the power spectrum data row is used to serve as the diagnostic pattern.

Then, the Fourier transform processing section 15b outputs the power spectrum data row thus created to the neural network 17 (step S305). Specifically, in the step S305, each of data contained in the power spectrum data row is inputted from the Fourier transform processing section 15b to a unit of the input layer of the neural network 17. This causes an output of an output value from the unit of the output layer of the neural network 17. The output value thus outputted is a result obtained by arithmetic processing of the neural network 17. Then, the output value is outputted from the neural network 17 to the determination processing section 18.

After that, the determination processing section 18 carries out, by using the output value of the neural network 17, a determination process for determining whether the diagnosis target has the abnormality or not (step S306). For example, in the step S306, the determination processing section 18 determines that the diagnostic target has the abnormality, in a case where the output value of the neural network 17 is close to "0", and determines that the diagnostic target has no abnormality, in a case where the output value of the neural network 17 is close to "1".

Then, the determination processing section 18 outputs a result of determining to the output section 20 (step S307).

In this way, the diagnostic operation of the diagnosis processing device 1 is finished.

Embodiment 2

Embodiment 2 of the present invention is described below. In Embodiment 1, the diagnosis processing device 1 checks the substantive feature of the abnormality of the diagnosis target by checking whether the diagnosis target in the chest radiograph has the abnormality or not.

On the other hand, in Embodiment 2, (i) whether a diagnosis target has abnormality or not and (ii) a name of a disease causing the abnormality of the diagnosis target are checked as feature contents of the abnormality of the diagnosis target.

Figure 14:
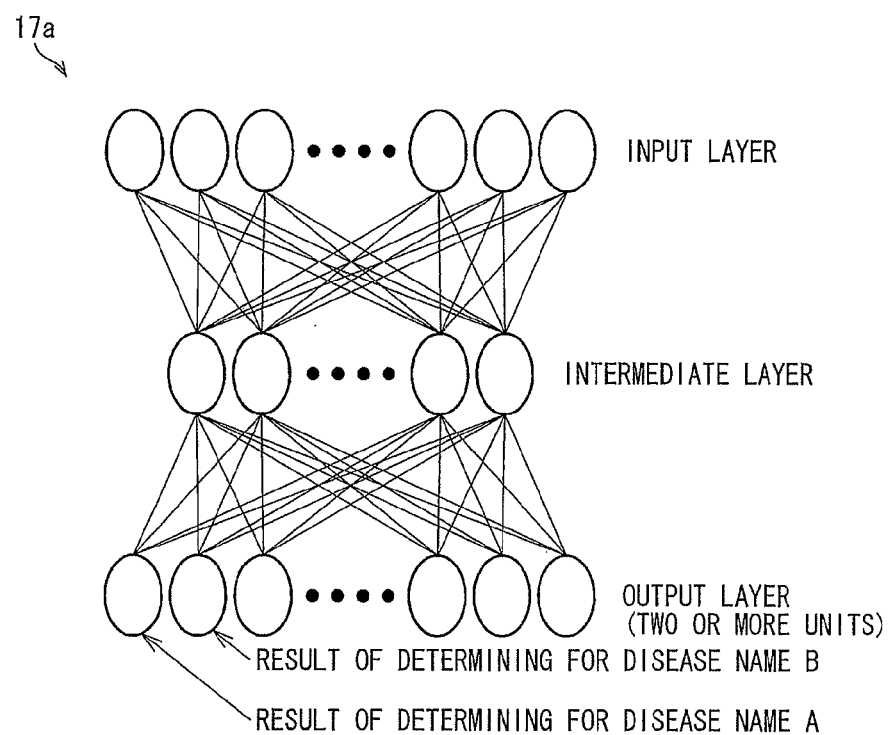
FIG. 14 is a view schematically showing an arrangement of a neural network used by a diagnosis processing device in accordance with another embodiment of the present invention.

A diagnosis processing device of the present embodiment and the diagnosis processing device 1 of Embodiment 1 are different from each other in that the diagnosis processing device of the present embodiment employs a neural network 17a shown in FIG. 14, whereas the diagnosis processing device of Embodiment 1 employs the neural network 17 shown in FIG. 5. The diagnosis device of the present embodiment is described below as to what is different from the diagnosis processing device 1 of Embodiment 1. That is, the diagnosis processing device of the present embodiment is not repeatedly described here as to what is similar to the diagnosis processing device 1 of Embodiment 1.

FIG. 14 is a view schematically showing an arrangement of the neural network 17a used by the diagnosis processing device of the present embodiment. As shown in FIG. 14, the neural network 17a is arranged such that output units of an output layer are provided so as to correspond to respective names of disease causing abnormalities of a diagnosis target, unlike the neural network 17 shown in FIG. 5.

For example, an identifier for an output unit is added to an output value from each of the unit of the output layer. In this case, the determination processing section 18 can identify, based on the identifier, from which unit of the output layer an output value of the output layer is outputted.

In the diagnosis processing device of the present embodiment, a learning image (for example, a chest radiograph) in which the following (i) and (ii) are pre-known is inputted to a learning pattern creating section 10a via an input layer 11, (i) abnormality information (abnormality presence-absence information) indicating whether the diagnosis target (for example, a right lung part) has abnormality or not and (ii) abnormality information (disease name information) indicating a name of a disease causing the abnormality of the diagnosis target.

It may be arranged that diagnosis information, in which neither abnormality presence/absence information nor disease name information is pre-known, is inputted to the diagnostic pattern creating section 10b via the input section 11, and that a learning processing section 21 causes neural network 17a's learning, by using a learning pattern for the learning image in which both of the abnormality information and the disease name information are pre-known.

For example, in the neural network 17a, a learning operation as described with reference to FIG. 2 in Embodiment 1 is carried out with respect to each of units of the output layer. Specifically, for a first unit corresponding to first disease name information (for example, disease name A), the learning pattern creating section 10a creates a learning pattern containing the first disease name information. Then, first unit's learning is carried out by use of the learning pattern.

Then, for a second unit corresponding to second disease name information (for example, a disease name B), the learning pattern creating section 10a creates a learning pattern containing the second disease information. Then, second unit's learning is carried out by use of the learning pattern.

In this way, each of the units of the output layer shown in FIG. 14 is subjected to learning.

In the diagnosis processing device of the present embodiment, it is possible to (i) check whether the diagnosis target has the abnormality or not and (ii), in a case where the diagnosis target has the abnormality, find the name of the disease causing the abnormality.

Figure 15:
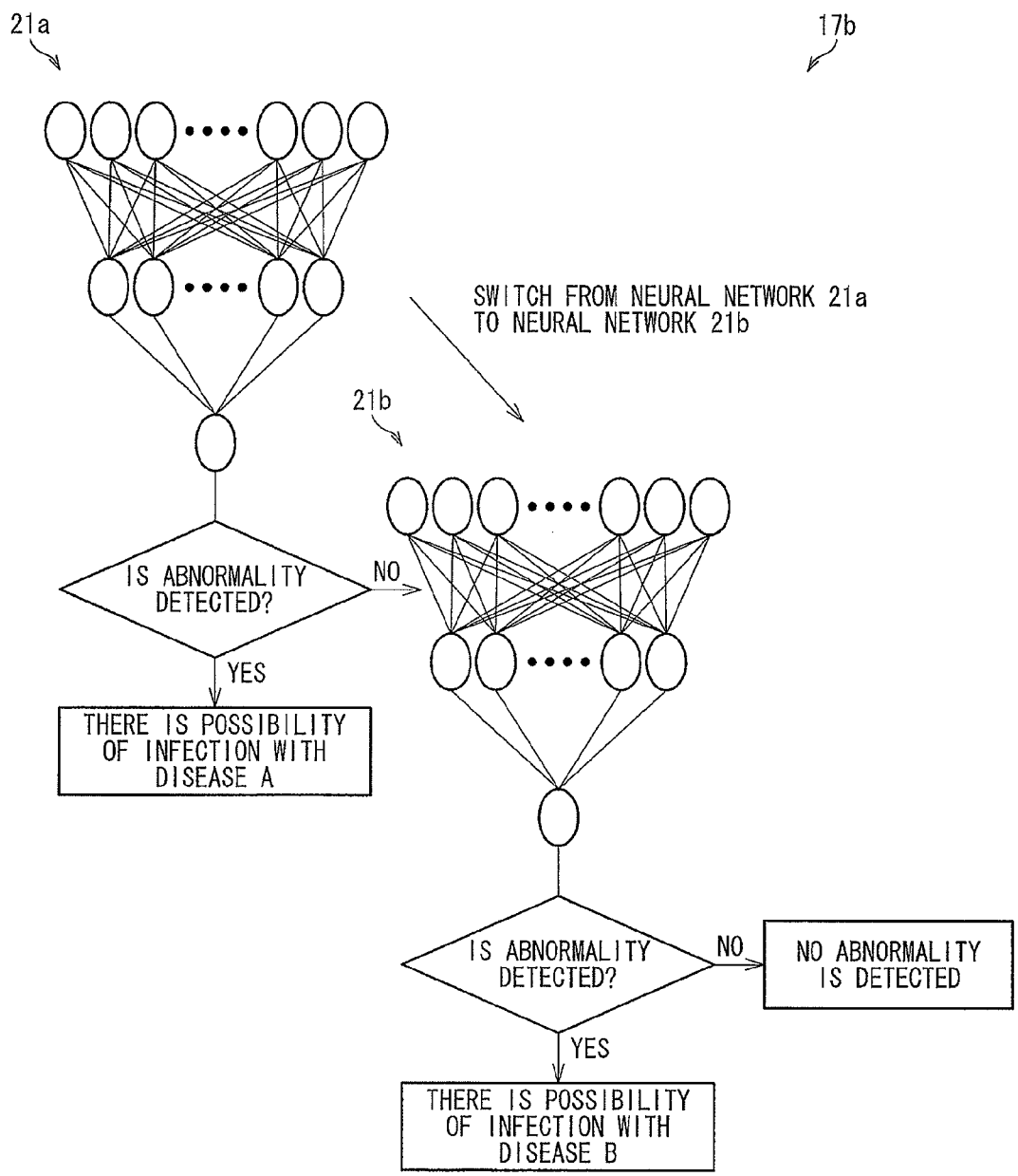
FIG. 15 is a view schematically showing an arrangement of a neural network used by the diagnosis processing device.

In the diagnosis processing device of the present embodiment, a neural network 17b shown in FIG. 15 may be used in replacement of the neural network 17a shown in FIG. 14. The neural network 17b shown in FIG. 15 includes neural networks 21a and 21b corresponding to respective disease names. In an example shown in FIG. 15, the neural network 21a corresponds to the disease name A and the neural network 21b corresponds to the disease name B, for example.

Like the neural network 17 shown in FIG. 5, each of the neural networks 21a and 21b is arranged such that an output layer includes one unit.

As shown in FIG. 15, for example, whether the diagnosis target has a symptom of the disease A or not is checked at first by using the neural network 21a. If a result of checking with the use of the neural network 21a demonstrates that the diagnosis target has the symptom of the disease A, then it is determined that there is a possibility of infection with the disease A.

In contrast, if the result of checking with the use of the neural network 21a demonstrates that the diagnosis target has no symptom of the disease A, then whether the diagnosis target has a symptom of the disease B or not is checked by using the neural network 21b.

If the result of checking with the use of the neural network 21b demonstrates that the diagnosis target has the symptom of the disease B, then it is determined that there is a possibility of infection with the disease B.

In contrast, if the result of checking with the use of the neural network 21b demonstrates that the diagnosis target has no symptom of the disease B, then it is determined that there is no infection with the diseases A and B.

The diagnosis processing device is, for example, connected to the neural network 21a via a known communications line such as the Internet at first, and sends and receives data to/from the neural network 21a.

After sending and receiving of the data to/from between the diagnosis processing device and the neural network 21a, a connection destination to which the diagnosis processing device is connected is switched from the neural network 21a to the neural network 21b.

This connects the diagnosis processing device to the neural network 21b via the communications line, so that the diagnosis processing device sends and receives data to/from the neural network 21b via the communications line.

Embodiment 3

Embodiment 3 of the present invention is described below. In Embodiment 3, neural networks as employed in the diagnosis processing device of Embodiment 2 are provided so as to correspond to respective corresponding human body parts.

Figure 16:
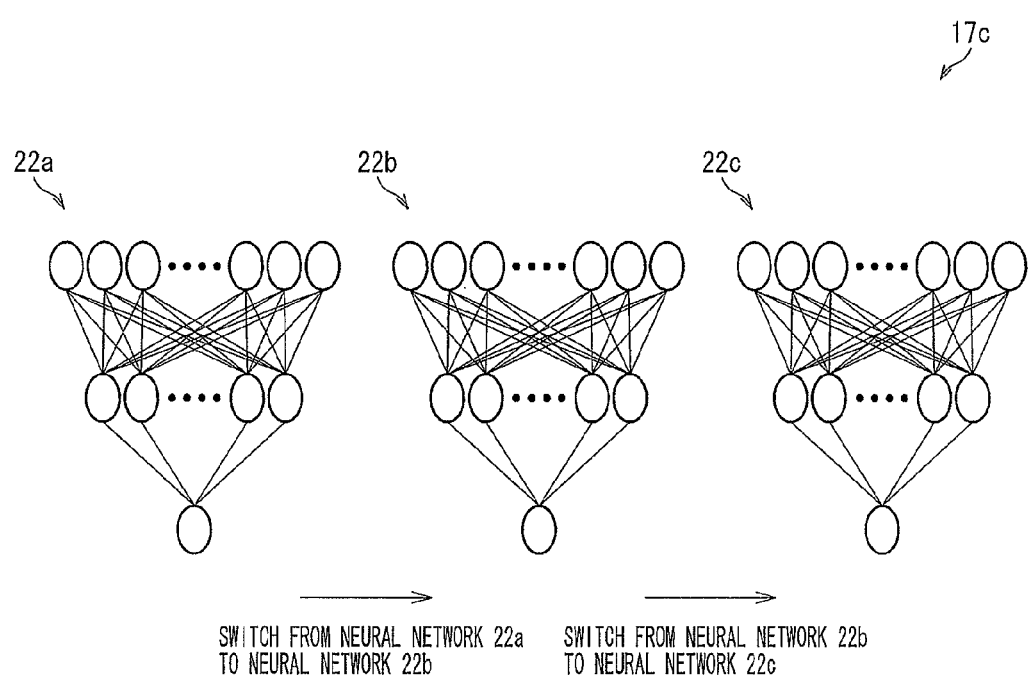
FIG. 16 is a view schematically showing an arrangement of a neural network used by the diagnosis processing device.

A diagnosis processing device of the present embodiment and the diagnosis processing device of Embodiment 2 are different from each other in that the diagnosis processing device of the present embodiment employs a neural network 17c shown in FIG. 16, whereas the diagnosis processing device of Embodiment 2 employs either the neural network 17a shown in FIG. 14 or the neural network 17b shown in FIG. 15. The diagnosis processing device of the present embodiment is described below as to what is different from the diagnosis processing device of Embodiment 2. Hence, the diagnosis processing device of the present embodiment is not described repeatedly here as to what is similar to the diagnosis processing device of Embodiment 2.

In the diagnosis processing device (a diagnosis processing system) of the present embodiment, the neural network 17c includes neural networks 22a through 22c each of which corresponds to a corresponding human body part. For example, the neural network 22a is used for (i) checking whether a human lung part has abnormality or not and (ii), in a case where the human lung part has the abnormality, finding a name of a disease causing the abnormality. The neural network 22b is used for (i) checking whether a human stomach part has abnormality or not and (ii), in a case where the human stomach part has the abnormality, finding a name of a disease causing the abnormality. The neural network 22c is used for (i) checking whether a human brain part has abnormality or not and (ii), in a case where the human brain part has the abnormality, finding a name of a disease causing the abnormality.

The diagnosis processing device of the present embodiment may be applied to obtain results of checking for various body parts. Further, the diagnosis processing device of the present embodiment may be applied in such a way that results of checking for human body parts for individual patients are personalized, for example. In this case, the results of checking for respective human body parts can be obtained for each patient. This makes it possible to understand a total condition of the body of the patient. As such, it is possible to build a diagnosis supporting system very useful to a doctor.

The diagnosis processing device is, for example, connected to the neural network 22a via a known communications line such as the Internet at first, and sends and receives data to/from the neural network 22a via the communications line.

After sending and receiving of data between the diagnosis processing device and the neural network 22a, a connection destination to which the diagnosis processing device is connected is switched from the neural network 22a to the neural network 22b.

This connects the diagnosis processing device to the neural network 22b via the communications line, so that the diagnosis processing device sends and receives data to/from the neural network 22b via the communications line.

After sending and receiving of the data between the diagnosis processing device and the neural network 22b, the connection destination to which the diagnosis processing device is connected is switched from the neural network 22b to the neural network 22c.

This ultimately connects the diagnosis processing device to the neural network 22c via the communications line, so that the diagnosis processing device sends and receives data to/from the neural network 22c via the communications line.

Embodiment 4

Figure 17:
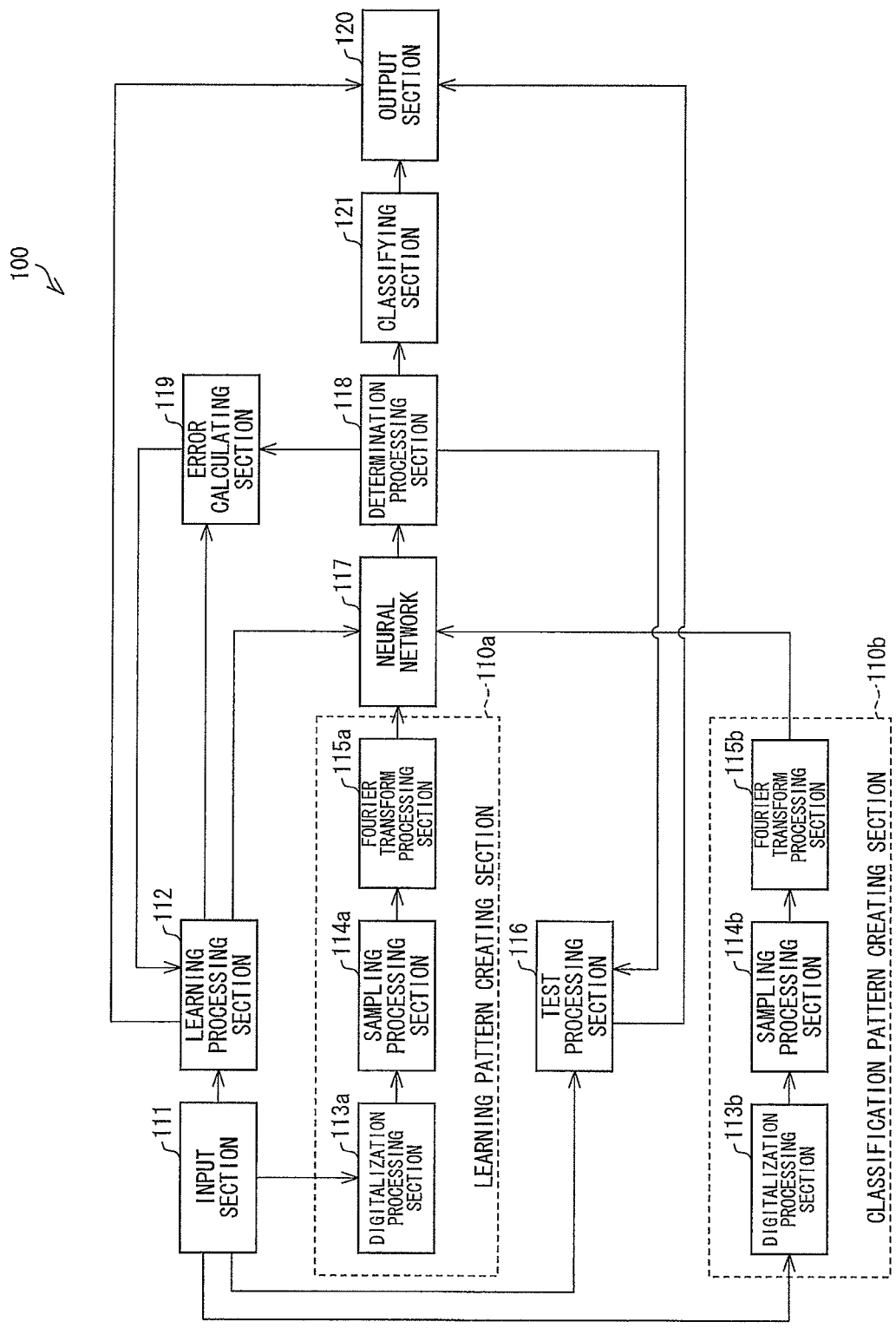
FIG. 17 is a block diagram schematically showing an arrangement of a classification processing device in accordance with another embodiment of the present invention.

Embodiment 4 of the present invention is described below. FIG. 17 is a block diagram schematically showing an arrangement of a classification processing device 100 in accordance with Embodiment 4 of the present invention.

As shown in FIG. 17, the classification processing device 100 is a classification processing device for classifying images to two or more groups in accordance with their patterns by use of a neural network 17, and the classification processing device 100 includes: a learning pattern creating section (learning pattern creating means) 110a for creating a learning pattern from a learning image, by (i) digitalizing the learning image into digital data, and (ii) sampling data from the digital data of the learning image by use of a predetermined sampling method, wherein the learning pattern indicates a data sequence of a sample data row of the data thus sampled, and the learning image is an image in which pattern information indicating a substantive feature of a pattern of the image is pre-known; a learning processing section (learning processing means) 112 for causing the neural network 117 to learn, by use of two or more learning patterns created as above by the learning pattern creating section 110a; a classification pattern creating section (classification pattern creating means) 110b for creating a classification pattern from a classification image, by (iii) digitalizing the classification image into digital data, and (iv) sampling data from the digital data of the classification image by use of the predetermined sampling method, wherein the classification pattern indicates a data sequence of a sample data row of the data thus sampled, and the classification image is an image in which pattern information is unknown; a determination processing section (determining means) 118 for determining a substantive feature of the pattern indicated in the pattern information in the classification image, based on an output value outputted, in response to an input of the classification pattern, from a learned neural network 117 which is the neural network 117 subjected to the learning; and a classifying section (classifying means) 121 for classifying the classification image to any of the two or more groups, based on a result of determining by the determination processing section 118.

In the classification processing device 100, the learning pattern creating section 110a (i) uses, as the learning image, the classification image in which the pattern information, which indicates the substantive feature of the pattern indicated in the pattern information in the classification image, is pre-known by a user, and (ii) digitalize the learning image into the digital data. Then, the learning pattern creating section 110a samples the data from the digital data of the learning image subjected by use of the predetermined sampling method such as, for example, a sampling method in which data of one longitudinal pixel row of an image are sampled. In this way, the learning pattern creating section 110a creates the learning pattern from the data thus sampled.

The learning processing section 112 causes the neural network 117's learning, by using two or more learning patterns created as such by the learning pattern creating section 110a. This causes the neural network 117 to become a learned neural network 117.

The classification pattern creating section 110b (i) digitalizes the classification image, in which the pattern information is unknown by the user, into the digital data and (ii) samples the data from the digital data of the classification image by use of the sampling method same as the sampling method used by the learning pattern creating section 110a. In this way, the classification pattern creating section 110b creates the classification pattern from the data thus sampled.

After an input of this classification pattern to the learned neural network 117 causes an output of an output value, the determination processing section 118 (i) determines, based on the output value, the substantive feature of the classification pattern indicated in the pattern information in the classification image, and (ii) outputs a result of determining to the classifying section 121.

In response, the classifying section 121 classifies the classification image into two or more groups, based on the result of determining.

In this way, the classification processing device 100 can (i) digitalize the classification image into the digital data, (ii) sample the data from the digital data of the classification images and create the classification pattern from the data thus sampled, and (iii) determine the substantive feature of the pattern indicated in the pattern information in the classification image.

Also, the classification processing device 100 can attain great reduction in load of arithmetic processing in the neural network 117. This is because, in the classification processing device 100, the arithmetic processing in the neural network 117 is carried out by use of a small amount of data sampled from the learning image.

The learning pattern creating section 110a includes a digitalization processing section 113a, a sampling processing section 114a, and a Fourier transform processing section 115a. Operations of the digitalization processing section 113a, the sampling processing section 114a, and the Fourier transform processing section 115a are similar to the operations of the digitalization processing section 13a, the sampling processing section 14a, and the Fourier transform processing section 15a shown in FIG. 1.

The classification pattern creating section 110b includes a digitalization processing section 113b, a sampling processing section 114b, and a Fourier transform processing section 115b. Operations of the digitalization processing section 113b, the sampling processing section 114b, and the Fourier transform processing section 115b are similar to the operations of the digitalization processing section 13b, the sampling processing section 14b, and the Fourier transform processing section 15b shown in FIG. 1.

Likewise, operations of an error calculating section 119 and an output section 120 are similar to the error calculating section 19 and the output section 20 shown in FIG. 1.

Figure 19:
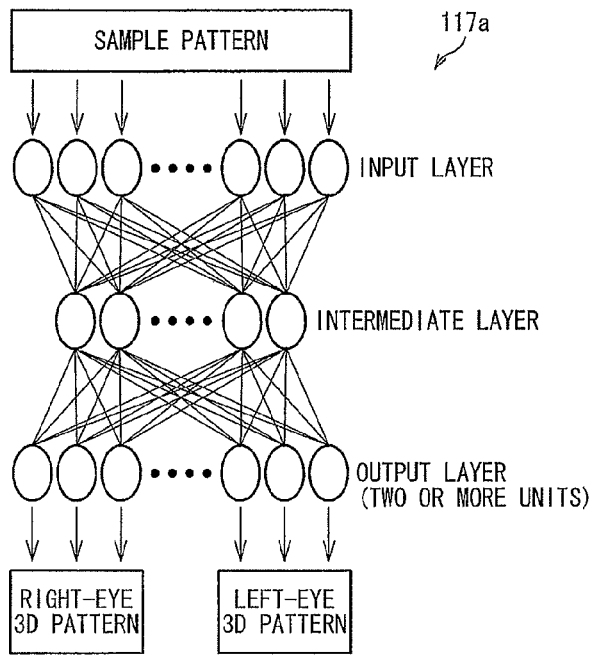
FIG. 19 is a view schematically showing an arrangement of a neural network used by the classification processing device.
Figure 20:
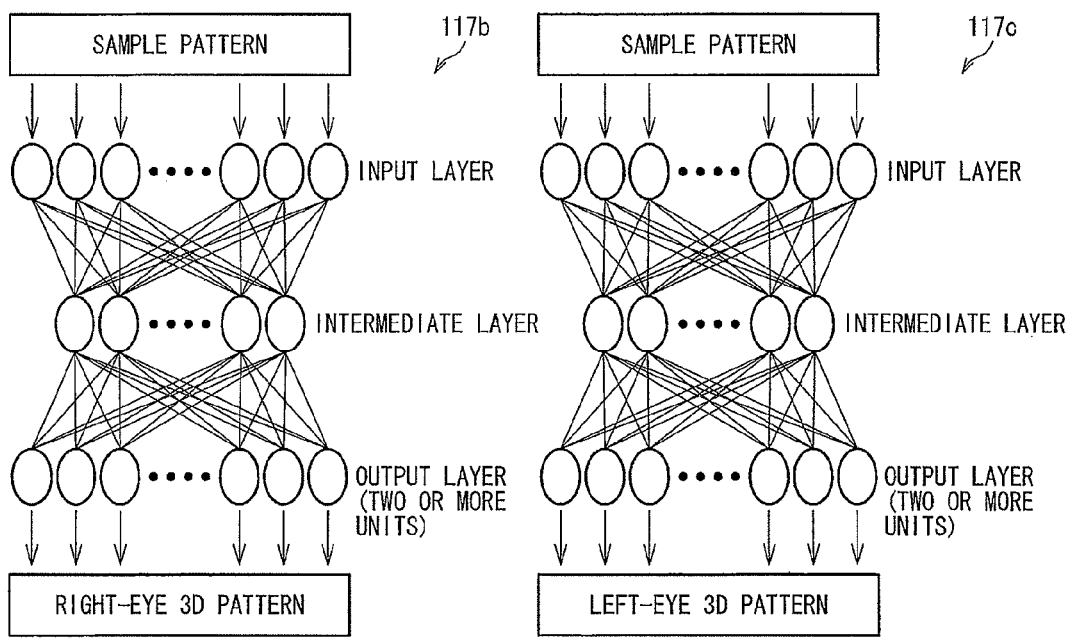
FIG. 20 is a view schematically showing an arrangement of a neural network used by the classification processing device.

The following describes a concrete example of the neural network 117 employed by the classification processing device 100. FIG. 19 shows one concrete example of the neural network 117.

In the classification processing device 100, the learning pattern creating section 110a (i) uses, as a learning image, a 2D image of which a 3D image is pre-known by a user, and (ii) carries out a digitalization process to the learning image. Then, the learning pattern creating section 110a samples data from the learning image subjected to the digitalization process, by using a predetermined sampling method such as, for example, a sampling method in which data of one longitudinal pixel row of an image are sampled. In this way, the learning pattern creating section 110a creates a learning pattern from the data thus sampled.

The learning processing section 112 causes neural network 117a's learning, by using two or more learning patterns created as such by the learning pattern creating section 110a. This causes a neural network 117a to become a learned neural network 117a.

The classification pattern creating section 110b (i) uses, as a classification image, a 2D image of which a 3D image is unknown by the user, (ii) carries out a digitalization process to the classification image, and (iii) samples data from the classification image subjected to the digitalization process, by using a sampling method same as the sampling method used by the learning pattern creating section 110a. In this way, the classification pattern creating section 110b creates a classification pattern from the data thus sampled.

After an input of the classification pattern to the learned neural network 117a causes an output of an output value, the determination processing section 118 (i) determines, based on the output value, a substantive feature of the classification pattern indicated in pattern information, and (ii) outputs a result of determining to the classifying section 121.

In response, the classifying section 121 classifies the 2D image to a 3D image (a right-eye image and a left-eye image), based on the result of determining.

The neural network 117a shown in FIG. 17 may be replaced with a right-eye neural network 117b and a left-eye neural network 117c.

The present invention is not limited to the embodiments above, but may be altered by a skilled person within the scope of the claims. That is, an embodiment derived from a proper combination of technical means disclosed in different embodiments is encompassed in the technical scope of the present invention.

Finally, the blocks of the diagnosis processing device 1 may be realized by way of hardware or software as executed by a CPU as follows.

The diagnosis processing device 1 includes a CPU (central processing unit) and memory devices (memory media). The CPU (central processing unit) executes instructions in control programs realizing the functions. The memory devices include a ROM (read only memory) which contains programs, a RAM (random access memory) to which the programs are loaded, and a memory containing the programs and various data. The objective of the present invention can also be achieved by mounting to the diagnosis processing device 1a computer-readable storage medium containing control program code (executable program, intermediate code program, or source program) for the diagnosis processing device 1 which is software realizing the aforementioned functions, in order for the computer (or CPU, MPU) to retrieve and execute the program code contained in the storage medium.

The storage medium may be, for example, a tape, such as a magnetic tape or a cassette tape; a magnetic disc, such as a Floppy (Registered Trademark) disc or a hard disc, or an optical disc, such as compact disc-ROM/MO/MD/digital video disc/compact disc-R; a card, such as an IC card (memory card) or an optical card; or a semiconductor memory, such as a mask ROM/EPROM/EEPROM/flash ROM.

The diagnosis processing device 1 may be arranged to be connectable to a communications network so that the program code may be delivered over the communications network. The communications network is not limited in any particular manner, and may be, for example, the Internet, an intranet, extranet, LAN, ISDN, VAN, CATV communications network, virtual dedicated network (virtual private network), telephone line network, mobile communications network, or satellite communications network. The transfer medium which makes up the communications network is not limited in any particular manner, and may be, for example, wired line, such as IEEE 1394, USB, electric power line, cable TV line, telephone line, or ADSL line; or wireless, such as infrared radiation (IrDA, remote control), Bluetooth (Registered Trademark), 802.11 wireless, HDR, mobile telephone network, satellite line, or terrestrial digital network. The present invention encompasses a carrier wave or data signal transmission in which the program code is embodied electronically. The present invention is made realizable in form of a computer data signal embedded in a carrier wave, on electric transmission of which computer data signal the program code is embodied.

A diagnosis processing device of the present invention is a diagnosis processing device for diagnosing a target for abnormality by use of a neural network, and includes: learning pattern creating means for creating a learning pattern by (i) digitalizing a learning image into digital data, the learning image being an image in which abnormality information indicating a substantive feature of the abnormality of the target is pre-known, and (ii) sampling data from the digital data of the learning image by use of a predetermined sampling method, the learning pattern indicating a data sequence of a sample data row of the data thus sampled; learning processing means for causing the neural network to learn, by use of two or more learning patterns created as above by the learning pattern creating means; diagnostic pattern creating means for creating a diagnostic pattern by (iii) digitalizing a diagnostic image into digital data, the diagnostic image being an image in which abnormality information is unknown, and (iv) sampling data from the digital data of the diagnostic image by use of the predetermined sampling method, the diagnostic pattern indicating a data sequence of a sample data row of the data thus sampled; and determining means for determining a substantive feature of the abnormality of the target indicated in the abnormality information in the diagnostic image, based on an output value outputted, in response to an input of the diagnostic pattern, from a learned neural network which is the neural network subjected to learning.

In the diagnosis processing device, the learning pattern creating means (i) uses, as the learning image, the diagnostic image in which the abnormality information indicating the substantive feature of the abnormality of the diagnosis target is pre-known by a user, and (ii) digitalize the learning image into the digital data. Then, the learning pattern samples the data from the digital data of the learning image by use of the predetermined sampling method. For example, in a case where reference directions are determined based on a shape feature of a diagnosis target part, which is the diagnosis target in the learning image, data are sampled from the learning image in a longitudinal direction out of the reference directions. Then, the learning pattern creating means creates the learning pattern from the data thus sampled.

The learning processing means causes the neural network's learning by use of the two or more learning patterns created by the learning pattern creating means. This causes the neural network to become the learned neural network.

The diagnostic pattern creating means (i) digitalizes the diagnostic image, in which the abnormality information is unknown by the user, into the digital data and (ii) samples the data from the digital data of the diagnostic image by use of the sampling method same as the sampling method used by the learning pattern creating means. Then, the diagnostic pattern creating mean's creates the diagnostic pattern from the data thus sampled.

After the input of the diagnostic pattern thus created to the learned neural network causes the output of the output value, the determining means determines, based on the output value, the substantive feature of the abnormality of the diagnosis target indicated in the abnormality information, and sends the result of determining to the user.

In this way, the diagnosis processing device can (i) digitalize the diagnostic image into the digital data, (ii) create the diagnostic pattern from the diagnostic image by sampling the data from the digital image of the diagnostic image, and (iii) determine, by using the diagnostic pattern thus created, the substantive feature of the abnormality of the diagnosis target indicated in the abnormality information.

This eliminates the need for an arrangement conventionally required for extracting of a suspicious region of interest from the diagnostic image in advance. As such, it is possible to realize the diagnosis processing device which has a simpler arrangement.

Conventionally, in order to extract the suspicious region of interest from the diagnostic image, it is necessary to collect entire data in the diagnostic image and use such large amount of the data. This gives a rise to a problem that load of arithmetic learning is very heavy.

In contrast, in the diagnosis processing device, it is not necessary to use the entire data. As such, it is possible to attain a great decrease in the load of the arithmetic processing. This is because, in the diagnosis processing device, it is possible to (i) create, for example, two or more patterns made up of respective two or more data rows sampled from the diagnostic image, (ii) carry out arithmetic processing of the neural network by using the two or more patterns thus created, and (iii), after the abnormality of the diagnosis target is detected by given arithmetic processing of the neural network, skip subsequent arithmetic processing of the neural network.

It is preferable that the predetermined sampling method includes determining (a) a region of the target in each of the learning image and the diagnostic image, and (b) at least one of a sampling direction, a sampling width, and a sampling interval of data sampling from the region of the target thus determined.

The arrangement allows efficient neural network's learning by determining the diagnosis target region and at least one of the sampling direction, the sampling width, and the sampling interval of data sampling from the diagnosis target region. As such, it is possible to improve an efficiency of the diagnostic process of the diagnosis processing device.

Generally, the sampling direction and the sampling width of the data sampling are same between a case where the learning pattern is created and a case where the diagnostic pattern is created. However, it is not necessary that the sampling interval is same between the above two cases. For example, when the learning pattern is created, it is suitable that data are sampled from a characteristic part of an image at broad intervals. On the other hand, when the diagnostic image is created, it is suitable that data sampling from an image is carried out at smaller intervals so that no data indicative of the abnormality of the diagnosis target fail to be sampled.

It is preferable that the predetermined sampling method includes setting the number of the learning patterns sampled from the learning image to a value smaller than the number of the diagnostic pattern sampled from the diagnostic image.

This makes it possible to efficiently create the sample pattern. Therefore, it is possible to speed up the learning operation of the neural network.

It is preferable that: the learning pattern creating means creates the learning pattern by Fourier transforming the data thus sampled from the learning image by using the predetermined sampling method, wherein the learning pattern indicates a data sequence of a power spectrum data row arranged in accordance with a frequency band pattern; and the diagnostic pattern creating means creates the diagnostic pattern by Fourier transforming the data thus sampled from the diagnostic image by using the predetermined sampling method, wherein the diagnostic pattern indicates a data sequence of a power spectrum data row arranged in accordance with a frequency band pattern.

Diligent study by the inventors has demonstrated that the arrangement improves detection accuracy of the neural network.

It is preferable that the diagnosis processing device further includes error calculating means for calculating errors between (x) substantive features of abnormalities indicated in abnormality information in the respective two or more learning patterns and (y) substantive features determined by the determining means, the substantive features (y) corresponding to the respective substantive features of abnormalities indicated in abnormality information in the respective two or more learning patterns, the neural network including an input layer, and intermediate layer, and an output layer connected in this order in a direction from an input layer side toward an output layer side, the neural network's learning being to weight connections between the input and intermediate layers and connections between the intermediate and output layers, so that an input of an input value to the input layer causes an output of a desired output value from the output layer, the learning processing means causing the neural network's learning in which the connections between the input and intermediate layers and the connections between the intermediate and output layers are weighted in such a manner that the errors calculated by the error calculating means are restored, so that the substantive features (y) are consistent with the respective corresponding substantive features of the abnormalities indicated in the abnormality information in the respective two or more learning patterns.

The arrangement can realize efficient neural network's learning. This is because the arrangement can cause the neural network to learn in such a manner that there is a restoration in errors between (i) the substantive features of abnormalities indicated in the pre-known abnormality information in the respective two or more learning patterns and (ii) the substantive features determined by the determining means.

It is preferable that the learning processing means repeats the neural network's learning until the errors calculated by the error calculating means become smaller than a predetermined threshold value.

The arrangement makes it possible to cause the neural network's learning by carrying out the size comparison of the errors calculated by the error calculating means with the predetermined threshold value. Therefore, it is possible to more efficiently carry out the neural network's learning.

It is preferable that, in a case where the number of times of the neural network's learning reaches a predetermined number before the errors calculated by the error calculating means become smaller than the predetermined threshold value, the learning processing means stops the neural network's learning.

With the arrangement, it is possible to stop the neural network's learning even in a case where the errors cannot become smaller than the predetermined threshold value. This makes it possible to avoid an unnecessary increase in the number of times of the neural network's learning.

It is preferable that the abnormality information contains abnormality presence/absence information indicating whether the target has the abnormality or not.

The arrangement makes it possible to determine whether the diagnosis target has the abnormality or not.

It is preferable that the abnormality information further contains disease name information indicating a name of a disease causing the abnormality of the target.

The arrangement makes it possible to determine the name of the disease causing the abnormality of the diagnosis target.

It is preferable that the output layer of the neural network includes two or more output layer units which correspond to respective two or more disease name information.

With the arrangement, it is not necessary to provide two or more neural networks corresponding to the respective two or more disease name information, and it is only necessary to provide the output layer made up of the two or more output layer units. Therefore, it is possible to check the two or more disease name information by use of the neural network having a relatively simple arrangement.

It is preferable that the neural network includes two or more neural networks corresponding to respective two or more disease name information.

This makes it possible to concurrently determine the two or more disease name information. In this case, it is possible to selectively determine any of the two or more disease name information. It is therefore possible to realize the diagnosis processing device capable of determining the two or more disease information in conformity with a user's request.

It is preferable that the diagnosis processing device further includes communicating means for sending and receiving data to/from the neural network by use of a communications line.

With the arrangement, it is not necessary to provide the neural network in the diagnosis processing device. This makes it possible to simplify an arrangement of the diagnosis processing device.

A diagnosis processing system of the present invention includes two or more diagnosis processing devices as early described, each of which two or more diagnosis processing devices is provided for diagnosing a target in a corresponding human body part for abnormality.

When used in a medical field, for example, the diagnosis processing system can determine the abnormality of the diagnosis target for each of different body parts of a patient. Therefore, it is possible to give a doctor a more useful diagnostic outcome.

A diagnosis processing method of the present invention is a diagnosis processing method for diagnosing a target for abnormality by use of a neural network, and includes: a learning pattern creating step of creating a learning pattern by (i) digitalizing a learning image into digital data, the learning image being an image in which abnormality information indicating a substantive feature of abnormality of the target is pre-known, and (ii) sampling data from the digital data of the learning image by use of a predetermined sampling method, the learning pattern indicating a data sequence of a sample data row of the data thus sampled; a learning processing step of causing a neural network to learn, by using two or more learning patterns created as such in the learning pattern creating step; a diagnostic pattern creating step of creating a diagnostic pattern by (iii) digitalizing a diagnostic image into digital data, the diagnostic image being an image in which abnormality information is unknown, and (iv) sampling data from the digital data of the diagnostic image by use of the predetermined sampling method, the diagnostic pattern indicating a data sequence of a sampling data row of the data thus sampled; and a determining step of determining a substantive feature of abnormality of the target indicated in the abnormality information in the diagnostic image, based on an output value outputted, in response to an input of the diagnostic pattern, from a learned neural network which is the neural network subjected to the learning in the learning processing step.

The diagnosis processing method (i) uses, as the learning image, the diagnostic image in which the abnormality information indicating the substantive feature of the abnormality of the diagnosis target is pre-known by a user, and (ii) digitalizes the learning image into the digital data. Then, the diagnosis processing method samples the data from the digital data of the learning image by use of the predetermined sampling method such as, for example, a sampling method in which data of one longitudinal pixel row of the learning image are sampled. Then, the diagnosis processing method creates the learning pattern from the data thus sampled.

Then, the diagnosis processing method causes the neural network's learning, by using the two or more learning patterns. This causes the neural network to become the learned neural network.

Then, the diagnosis processing method (i) digitalizes the diagnostic image in which the abnormality information is unknown by the user, and (ii) samples data from the digital data of the diagnostic image by use of the sampling method same as the sampling method used for creating the learning pattern. Then, the diagnosis processing method creates the diagnostic pattern from the data thus sampled.

After the input of the diagnostic pattern to the learned neural network causes the output of the output value, the diagnosis processing method (i) determines, based on the output value of the learned neural network, the substantive feature of the abnormality of the diagnosis target indicated in the abnormality information, and (ii) gives the user a result of checking.

The diagnosis processing method thus can (i) digitalize the diagnostic image into the digital data, (ii) sample data from the digital data of the diagnostic image and create the diagnostic pattern from the data thus sampled, and (iii) determine, by using the diagnostic pattern, the substantive feature of the abnormality of the diagnosis target indicated in the abnormality information.

This eliminates the need for an arrangement conventionally required for extracting of a suspicious region of interest from a diagnostic image in advance. As such, it is possible to determine the substantive feature of the abnormality of the diagnosis target indicated in the abnormality information, by using a simpler arrangement.

Conventionally, in order to extract the suspicious region of interest from the diagnostic image, it is necessary to collect entire data in the diagnostic image and use such large amount of the data. This gives a rise to a problem that load of arithmetic processing is heavy.

In contrast, in the diagnosis processing device, it is not necessary to use the entire data. As such, it is possible to attain a great decrease in load of arithmetic processing. This is because, in the diagnosis processing device, it is possible to (i) create, for example, the two or more patterns made up of the respective two or more data rows sampled from the diagnostic image, (ii) carry out arithmetic processing one after another by using the two or more patterns thus created, and (iii), when the abnormality of the diagnosis target is detected by given arithmetic processing, skip subsequent arithmetic processing.

The diagnosis processing device may be realized on a computer. In this case, the scope of the present invention encompasses a diagnosis processing program for realizing the diagnosis processing device on the computer by causing the computer to operate as each means. The scope of the present invention also encompasses a computer-readable storage medium in which the diagnosis processing program is stored.

A classification processing device of the present invention is a classification processing device for classifying images to two or more groups in accordance with their patterns by use of a neural network, and includes: learning pattern creating means for creating a learning pattern by (i) digitalizing a learning image into digital data, the learning image being an image in which pattern information indicating a substantive feature of a pattern of the image is pre-known, and (ii) sampling data from the digital data of the learning image by use of a predetermined sampling method, the learning pattern indicating a data sequence of a sample data row of the data thus sampled; learning processing means for causing the neural network to learn, by use of two or more learning patterns created as above by the learning pattern creating means; classification pattern creating means for creating a classification pattern by (iii) digitalizing a classification image into digital data, the classification image being an image in which pattern information is unknown, and (iv) sampling data from the digital data of the classification image by use of the predetermined sampling method, the classification pattern indicating a data sequence of a sample data row of the data thus sampled; determining means for determining a substantive feature of the pattern indicated in the pattern information in the classification image, based on an output value outputted, in response to an input of the classification pattern, from a learned neural network which is the neural network subjected to the learning; and classifying means for classifying the classification image to any of the two or more groups, based on a result of determining by the determining means.

In the classification processing device, the learning pattern creating means (i) uses, as the learning image, the classification image in which the pattern information indicating the substantive feature of the pattern indicated in the classification image is pre-known by a user, and (ii) digitalizes the learning image into the digital data. Then, the learning pattern creating means samples the data from the digital data of the learning image by use of the predetermined sampling method such as, for example, a sampling method in which data of one longitudinal pixel row of an image is sampled. Then, the learning pattern creating means creates the learning pattern from the data thus sampled.

The learning processing means causes the neural network's learning, by using the two or more learning patterns created by the learning pattern creating means. This causes the neural network to become the learned neural network.

The classification pattern creating means (i) digitalizes the classification image, in which the pattern information is unknown by the user, into the digital data and (ii) samples the data from the digital data of the classification image by use of the sampling method same as the sampling method used by the learning pattern creating means. The classification pattern creating means creates the classification pattern from the data thus sampled.

After an input of the classification pattern thus created to the learned neural network causes an output of an output value, the determining means determines, based on the output value, the substantive feature of the pattern indicated in the pattern information, and outputs a result of determining to the classifying means.

In response, the classifying means classifies the images into any of the tow or more groups, based on the result of determining thus received.

The classification processing device thus can (i) digitalize the classification image into the digital data, (ii) sample the data from the digital data of the classification image and create the classification pattern from the data thus sampled, and (iii) check the substantive feature of the classification pattern indicated in the pattern information in the classification image.

Further, the classification processing device is capable of (i) causing arithmetic processing in the neural network by using data sampled from an image, (ii) stopping the arithmetic processing after outcomes sufficient for decision making are obtained, and (iii) skipping subsequent arithmetic processing. This can attain a great decrease in load of the arithmetic processing of the neural network.

The present invention can provide (i) a diagnosis processing device, (ii) a diagnosis processing system, (iii) a diagnosis processing method, (iv) a diagnosis processing program, (v) a computer-readable storage medium storing therein the diagnosis processing program, and (vi) a classification processing device, each of which (i) through (vi) makes it possible to accurately and easily detect abnormality by image diagnosis.

REFERENCE SIGNS LIST

1: diagnosis processing device
10$a$, 110$a$: learning pattern creating section (learning pattern creating means)
10$b$: diagnostic pattern creating section (diagnostic pattern creating means)
11, 111: input section
12, 112: learning processing section (learning processing means)
13$a$, 13$b$, 113$a$, 113$b$: digitalization processing section
14$a$, 14$b$, 114$a$, 114$b$: sampling processing section
15$a$, 15$b$, 115$a$, 115$b$: Fourier transform processing section
16, 116: test processing section
17, 17$a$, 17$b$, 17$c$, 21$a$, 21$b$, 22$a$, 22$b$, 22$c$, 117, 117$a$, 117$b$, 117$c$: neural network
18, 118: determination processing section (determining means)
19, 119: error calculating section (error calculating means)
20, 120: output section
31: communicating section (communicating means)

50: communications line
100: classification processing device
110b: classification pattern creating section (classification pattern creating means)
121: classifying section (classifying means)

The invention claimed is:

1. A diagnosis processing device for diagnosing a target for abnormality by use of a neural network, the diagnosis processing device comprising:
   a learning pattern creating section for creating a learning pattern by (i) digitalizing a learning image into digital data, the learning image being an image in which abnormality information indicating a substantive feature of abnormality of the target is pre-known, and (ii) without extracting data of a possible abnormal site from the target, sampling data from the digital data of the learning image by use of a predetermined sampling method, the learning pattern indicating a data sequence of a sample data row of the data thus sampled;
   a learning processing section for causing the neural network to learn, by use of two or more learning patterns created as above by the learning pattern creating section;
   a diagnostic pattern creating section for creating a diagnostic pattern by (iii) digitalizing a diagnostic image into digital data, the diagnostic image being an image in which abnormality information is unknown, and (iv) without extracting data of a possible abnormal site from the target, sampling data from the digital data of the diagnostic image by use of the predetermined sampling method, the diagnostic pattern indicating a data sequence of a sample data row of the data thus sampled; and
   a determining section for determining a substantive feature of the abnormality of the target indicated in the abnormality information in the diagnostic image, based on an output value outputted, in response to an input of the diagnostic pattern, from a learned neural network which is the neural network subjected to learning.

2. The diagnosis processing device as set forth in claim 1, wherein
   the predetermined sampling method includes determining (a) a region of the target in each of the learning image and the diagnostic image, and (b) at least one of a sampling direction, a sampling width, and a sampling interval of data sampling from the region of the target thus determined.

3. The diagnosis processing device as set forth in claim 1, wherein
   the predetermined sampling method includes setting the number of the learning patterns sampled from the learning image to a value smaller than the number of the diagnostic pattern sampled from the diagnostic image.

4. The diagnosis processing device as set forth in claim 1, wherein:
   the learning pattern creating section creates the learning pattern by Fourier transforming the data thus sampled from the learning image by using the predetermined sampling method, wherein the learning pattern indicates a data sequence of a power spectrum data row arranged in accordance with a frequency band pattern; and
   the diagnostic pattern creating section creates the diagnostic pattern by Fourier transforming the data thus sampled from the diagnostic image by using the predetermined sampling method, wherein the diagnostic pattern indicates a data sequence of a power spectrum data row arranged in accordance with a frequency band pattern.

5. The diagnosis processing device as set forth in claim 1, further comprising
   an error calculating section for calculating errors between (x) substantive features of abnormalities indicated in abnormality information in the respective two or more learning patterns and (y) substantive features determined by the determining section, the substantive features (y) corresponding to the respective substantive features of abnormalities indicated in abnormality information in the respective two or more learning patterns,
   the neural network including an input layer, and intermediate layer, and an output layer connected in this order in a direction from an input layer side toward an output layer side,
   the neural network's learning being to weight connections between the input and intermediate layers and connections between the intermediate and output layers, so that an input of an input value to the input layer causes an output of a desired output value from the output layer,
   the learning processing section causing the neural network's learning in which the connections between the input and intermediate layers and the connections between the intermediate and output layers are weighted in such a manner that the errors calculated by the error calculating section are restored, so that the substantive features (y) are consistent with the respective corresponding substantive features of the abnormalities indicated in the abnormality information in the respective two or more learning patterns.

6. The diagnosis processing device as set forth in claim 5, wherein
   the learning processing section repeats the neural network's learning until the errors calculated by the error calculating section become smaller than a predetermined threshold value.

7. The diagnosis processing device as set forth in claim 6, wherein
   in a case where the number of times of the neural network's learning reaches a predetermined number before the errors calculated by the error calculating section become smaller than the predetermined threshold value, the learning processing section stops the neural network's learning.

8. The diagnosis processing device as set forth in claim 1, wherein
   the abnormality information contains abnormality presence/absence information indicating whether the target has the abnormality or not.

9. The diagnosis processing device as set forth in claim 8, wherein
   the abnormality information further contains disease name information indicating a name of a disease causing the abnormality of the target.

10. The diagnosis processing device as set forth in claim 9, wherein
    the output layer of the neural network includes two or more output layer units which correspond to respective two or more disease name information.

11. The diagnosis processing device as set forth in claim 9, wherein
    the neural network includes two or more neural networks corresponding to respective two or more disease name information.

12. The diagnosis processing device as set forth in claim 1, further comprising a communicating section for sending and receiving data to/from the neural network by use of a communications line.

13. A diagnosis processing system, comprising two or more diagnosis processing devices as set forth in claim 1, each of which two or more diagnosis processing devices is provided for diagnosing a target in a corresponding human body part for abnormality.

14. A non-transitory computer readable storage medium in which a diagnosis processing program for causing a computer to operate as the means of the diagnosis processing device as set forth in claim 1 is stored.

15. A diagnosis processing method for diagnosing a target for abnormality by use of a neural network, the diagnosis processing method comprising:

a learning pattern creating step of creating a learning pattern by (i) digitalizing a learning image into digital data, the learning image being an image in which abnormality information indicating a substantive feature of abnormality of the target is pre-known, and (ii) without extracting data of a possible abnormal site from the target, sampling data from the digital data of the learning image by use of a predetermined sampling method, the learning pattern indicating a data sequence of a sample data row of the data thus sampled;

a learning processing step of causing a neural network to learn, by using two or more learning patterns created as such in the learning pattern creating step;

a diagnostic pattern creating step of creating a diagnostic pattern by (iii) digitalizing a diagnostic image into digital data, the diagnostic image being an image in which abnormality information is unknown, and (iv) without extracting data of a possible abnormal site from the target, sampling data from the digital data of the diagnostic image by use of the predetermined sampling method, the diagnostic pattern indicating a data sequence of a sample data row of the data thus sampled; and a determining step of determining a substantive feature of abnormality of the target indicated in the abnormality information in the diagnostic image, based on an output value outputted, in response to an input of the diagnostic pattern, from a learned neural network which is the neural network subjected to the learning in the learning processing step.

16. A classification processing device for classifying images to two or more groups in accordance with their patterns by use of a neural network, the classification processing device comprising:

a learning pattern creating section for creating a learning pattern by (i) digitalizing a learning image into digital data, the learning image being an image in which pattern information indicating a substantive feature of a pattern of the image is pre-known, and (ii) without extracting data of a possible site having the pattern from the image, sampling data from the digital data of the learning image by use of a predetermined sampling method, the learning pattern indicating a data sequence of a sample data row of the data thus sampled;

a learning processing section for causing the neural network to learn, by use of two or more learning patterns created as above by the learning pattern creating section;

a classification pattern creating section for creating a classification pattern by (iii) digitalizing a classification image into digital data, the classification image being an image in which pattern information is unknown, and (iv) without extracting data of a possible site having the pattern from the image, sampling data from the digital data of the classification image by use of the predetermined sampling method, the classification pattern indicating a data sequence of a sample data row of the data thus sampled;

a determining section for determining a substantive feature of the pattern indicated in the pattern information in the classification image, based on an output value outputted, in response to an input of the classification pattern, from a learned neural network which is the neural network subjected to the learning; and a classifying section for classifying the classification image to any of the two or more groups, based on a result of determining by the determining section.

\* \* \* \* \*